(12) United States Patent
Kettner et al.

(10) Patent No.: US 6,586,615 B1
(45) Date of Patent: Jul. 1, 2003

(54) α-AMINOBORONIC ACIDS PREPARED BY NOVEL SYNTHETIC METHODS

(75) Inventors: Charles A. Kettner, Wilmington, DE (US); Sharada Jagannathan, Wilmington, DE (US); Timothy Patrick Forsyth, San Mateo, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/043,865

(22) Filed: Jan. 9, 2002

Related U.S. Application Data

(60) Provisional application No. 60/260,719, filed on Jan. 10, 2001.

(51) Int. Cl.[7] .................................................. C07F 5/04
(52) U.S. Cl. ...................................... 558/288; 558/298
(58) Field of Search ................................ 558/286, 287, 558/288, 298

(56) References Cited

U.S. PATENT DOCUMENTS

| | | | |
|---|---|---|---|
| 4,499,082 A | | 2/1985 | Shenvi et al. |
| 4,537,773 A | * | 8/1985 | Shenvi .......................... 514/63 |
| 5,169,841 A | * | 12/1992 | Kleeman et al. ................ 514/2 |
| 5,187,157 A | | 2/1993 | Kettner et al. |
| 5,250,720 A | * | 10/1993 | Kettner et al. ............... 558/288 |
| 5,384,410 A | | 1/1995 | Kettner |
| 5,462,964 A | | 10/1995 | Fevig et al. |
| 5,543,526 A | * | 8/1996 | Mallart et al. ............... 548/110 |
| 5,639,739 A | | 6/1997 | Dominguez et al. |
| 5,658,885 A | * | 8/1997 | Lee et al. ...................... 514/13 |
| 5,698,538 A | * | 12/1997 | Amparo et al. ................ 514/64 |
| 5,814,622 A | * | 9/1998 | de Nanteuil et al. .......... 514/64 |

FOREIGN PATENT DOCUMENTS

| | | |
|---|---|---|
| WO | WO 01002424 | 1/2001 |
| WO | WO 01007407 | 2/2001 |

OTHER PUBLICATIONS

CA:127:95617 abs of FR2739858 Apr. 1997.*
Jagannathan et al, J. Org. Chem., vol. 66, 2001, pp. 6375–6380.
Mantri et al, J. Org. Chem. 61 5690–5692, 1996.
Matteson, Chem. Rev. 89, 1538–1551, 1989.
Scriven & Turnbull, Chem. Reviews 88, 298–360, 1988.
Matteson & Beedle, Tetrahedron Letters 28, 4499–4502, 1987.
Matteson et al, J. Am. Chem. Soc. 108 810–819, 1986.
Sadhu & Matteson Organometallics 4, 1687–1689, 1985.
Kinder et al, J. Med. Chem. 28, 1917–1925, 1985.
Laganis & Chenard, Tetrahedron Letters 25, 5831–5834, 1984.
Matteson et al, Organometallics 3, 1284–1288, 1984.
Kettner & Shenvi, J. Biol. Chem. 259, 15106–15114, 1984.
Matteson & Arne, Organometallics 1, 280–288, 1982.
Matteson, J. Am. Chem. Soc., 103, 5241–5242, 1981.
Matteson, J. Organometallic Chem. 170, 259–264, 1979.
Middleton, J. Org. Chem. 40, 574–578, 1975.
Koehler & Lienhard, Biochemistry 10, 2477–2483, 1971.
Antonov et al, FEBS Lett. 7, 23, 1970.
Taliana et al, Analytical Biochemistry, 240, 60–67, 1996.

* cited by examiner

*Primary Examiner*—Jean F. Vollano

(57) ABSTRACT

The present invention relates to a novel class of α-aminoboronic acids of Formula (V),

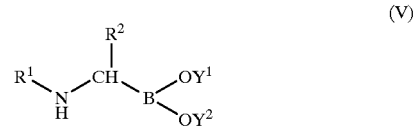

which are useful as intermediates in synthetic processes for inhibitors of the serine proteases, leukocyte elastase, pancreatic elastase, cathepsin G, and chymotrypsin. More specifically, the α-aminoboronic acids are useful as intermediates for the synthesis of Hepatitis C Virus (HCV) protease inhibitors. This invention also generally relates to novel methods for the preparation of α-aminoboronic acids.

21 Claims, No Drawings

α-AMINOBORONIC ACIDS PREPARED BY NOVEL SYNTHETIC METHODS

This application claims benefit of U.S. Provisional Application No. 60/260,719 filed Jan. 10, 2001.

FIELD OF THE INVENTION

The present invention relates to a novel class of α-aminoboronic acids, which are useful as intermediates in synthetic processes for boronic acid inhibitors of the serine proteases, leukocyte elastase, pancreatic elastase, cathepsin G, and chymotrypsin. More specifically, the α-aminoboronic acids are useful as intermediates for the synthesis of Hepatitis C Virus (HCV) protease inhibitors. This invention also generally relates to novel methods for the preparation of α-aminoboronic acids.

BACKGROUND OF THE INVENTION

Inhibitors of HCV protease have been prepared by replacing the scissile bond cleaved in peptide substrates with electrophillic groups. Of the various electrophilic groups examined, boronic acids have a distinct advantage. The concept of using boronic acids as serine protease inhibitors was introduced in the early 70's Antonov et al. *FEBS Lett* 7, 23 (1970); Koelhler and Lienhard *Biochemistry* 10, 2477–2483 (1971). An α-aminoboronic acids, Ac-boroPhe-OH, was first prepared by Matteson *J. Am. Chem. Soc.* 103, 5241–5242 (1981). This compound inhibits chymotrypsin with a $K_i$ of 2.1 μM. Kettner and Shenvi *J. Biol. Chem.* 259, 15106–15114 (1984) were able to couple α-aminoboronic acids to peptides and were able to show that they were very effective inhibitors of the serine proteases, leukocyte elastase, pancreatic elastase, cathepsin G, and chymotrypsin. Their specificity was highly dependent on the nature of the side chain of the α-aminoboronic acid. These initial compounds are described in U.S. Pat. No. 4,499,082 (1985). U.S. Pat. No. 4,499,082 also discloses the use of side chain protected amino acids and equivalent amino acids known to those skilled in the art. More recent patents cover peptide boronic acids containing basic side chains. U.S. Pat. No. 5,187,157 discloses boronic acid inhibitors specially designed as inhibitors of trypsin-like serine proteases. U.S. Pat. No. 5,658,885 (1997) discloses boronic acid inhibitors containing the following side chains: $C_1$–$C_{12}$-alkyl substituted with —NHC(NH)H, —ONHR$_6$, or —ONHC(NH)NHR$_6$ as well as phenylalanine analog substituted with a cyano group. Other boronic acid inhibitors containing basic sidechain are disclosed in Fevig et al U.S. Pat. No. 5,462,964 (1995), Dominguez et al. U.S. Pat. No. 5,639,739 (1997) and Amparo et al. U.S. Pat. No. 5,698,538 (1997). Additionally, boronic acid inhibitors of Hepatitis C Virus (HCV) protease are disclosed in Kettner et al PCT Publication WO 01/02424 (Jan. 11, 2001).

Schemes 1A, 1B and 1C outline the different approaches that have been used in the synthesis of α-aminoboronic acids containing a variety of sidechains. These include compounds where R is alkyl, aryl, and alkylaryl containing various degrees of unsaturation.

In Scheme 1A, a Grignard reagent or other suitable nucleophile is added to a trialkyl boronate to give a substituted dialkyl boronate. Transesterification with a suitable diol protecting group gives the boronate ester 2. 2 is shown protected as the pinanediol ester, however, pinacol or $C_2$ symmetrical diol, such as (R,R)2,3-butandiol, and (R,R) dicyclohexaneethanediol can also be used effectively. The α-chloroalkyl intermediate 3 is obtained by the nucleophilic addition of the anion of methylene chloride to the boronic acid ester. Nucleophilic additions to boronates are generally performed under harsh conditions and sub-zero temperatures. 3 is treated with the lithium salt of hexamethyldisilazane to give the bis-silane protected amine 4. Compound 4 is treated with either anhydrous HCl or trifluoroacetic acid to give the amine 5 as a hydrochloride salt or trifluoroacetate salt. For example of Scheme 1A see U.S. Pat. No. 4,499,082 (1985).

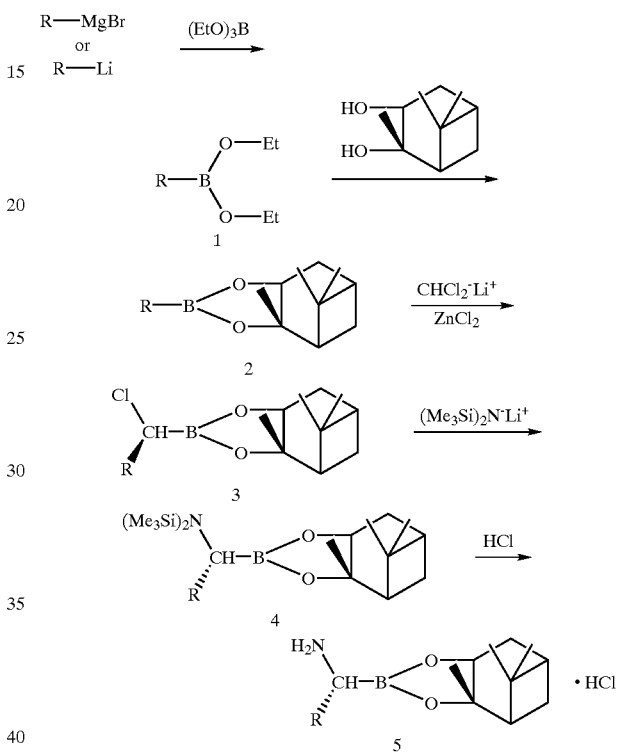

Scheme 1B shows the introduction of an alkyl sidechain as an olefin (see Matteson et al. *Organometallics* 3, 1284–1288, 1984 and U.S. Pat. No. 5,187,157, 1993). Hydroboration with catacholborane give the alkyl boronate. After transesterification with pinanediol, compound 2 is obtained. For example hydroboration of 3-bromopropene provide a 3-bromopropyl sidechain intermediate. These reactions are amenable for nucleophilic additions but not for electrophilic additions.

Scheme 1B

-continued

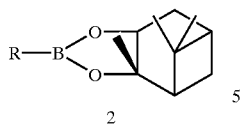

2

Scheme 1C shows the preparation of α,α-dichloromethyl boronate ester 7, which then allows the nucleophilic addition of a sidechain to give 3 (see Kinder et al *J. Med. Chem.* 28, 1917–1925, 1985). The presence of acidic protons in reagents diminishes their ability to undergo nucleophilic addition reactions.

Scheme 1C

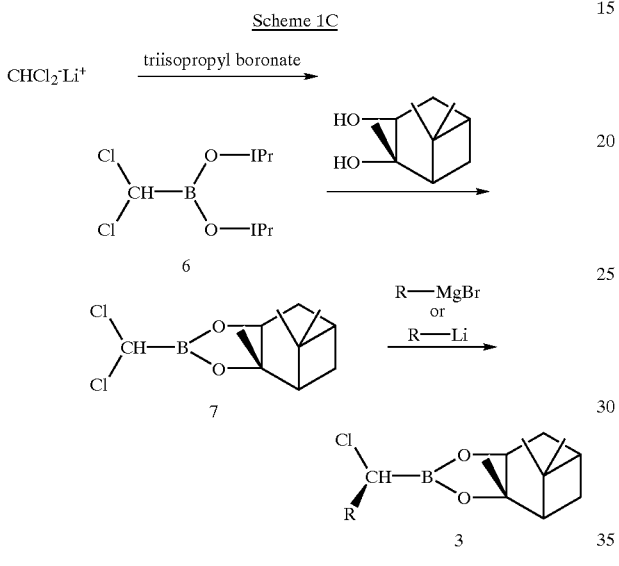

Although, the procedures in Schemes 1A, 1B and 1C allow the synthesis of a number of α-aminoboronic acids, there are limitations on this chemistry for the preparation of α-aminoboronic acids of the present invention. First, a stable nucleophile or olefin must be available for generation of 2. Second, the sidechain of 2 must be stable to the harsh reaction conditions (highly basic and sub-zero temperatures) required to convert 2 to 3. These reaction conditions are not amenable to hydrocarbons containing electrophilic centers.

None of the above-cited references provide methods for introducing boroaminoacid sidechains as electrophiles. The present invention provides a novel procedure as shown herein that allows the synthesis of α-aminoboronic acids with primary or secondary amino groups required for the preparation of aminoboronic acids peptides with versatile sidechains. The present invention provides synthesis of novel α-aminoboronic acid by introducing sidechains as electrophiles such as 2,2-difluoro-1-bromoethane, 3,3,3-trifluoro-1-bromopropane, and 2-bromoacetate esters. Similarly, sidechains can be introduced as olefins, wherein the harsh conditions such as treatment with the anion of methylene chloride are avoided. The sequence of reactions of the present invention has made it possible to prepare structurally diverse α-aminoboronic acids. In addition to the specific compounds demonstrated in the present invention, higher order acrylates or alkyl halides can be used to give more complex sidechains. This is particularly valuable for the preparation of compounds with sidechains containing sensitive groups such as ketones, phosphonates and sulfonamides.

SUMMARY OF THE INVENTION

The present invention concerns novel processes for the preparation of α-aminoboronic acids which are useful as HCV protease inhibitors.

There is provided by this invention a process for preparation of a compound of Formula (V):

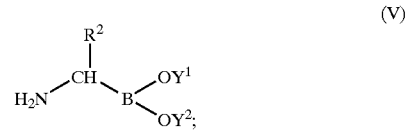

(V)

wherein:
$R^2$ is $-CH_2(CH_2)_mW$, $-CH_2(C=O)R^5$, $-CH_2CH_2(C=O)R^5$, $-CHR^4(CR^{4a}R^3)_mW$, $-CHR^{4a}(C=O)R^5$, $-CHR^4CHR^{4a}(C=O)R^5$, $-CHR^{4a}(P=O)(R^6)_2$, $-CHR^4CHR^{4a}(P=O)(OR^6)_2$, $-CHR^{4a}SO_2NH_2-$ $CHR^4CHR^{4a}SO_2NH_2$, $-CHR^{4a}SO_3R^6$, $-CHR^4CHR^{4a}SO_3R^6$;

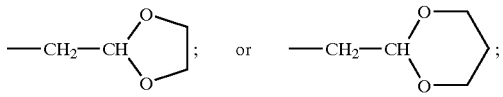

$R^3$ is H, F, Cl or Br;
m is 0–4;
W is $-CH_2F$, $-CHF_2$, $-CF_3$, $-CH_2Cl$, $-CHCl_2$, or $-CCl_3$;
$R^4$ and $R^{4a}$ are independently H or $C_1-C_6$ alkyl, aryl, or aryl-$C_1-C_6$ alkyl-;
$R^5$ is $C_1-C_6$ alkyl, aryl, aryl-$C_1-C_6$ alkyl-, $-OR^6$, $-NH_2$, $-N(R^6)_2$, or $-NHR^6$;
$R^6$ is $C_1-C_6$ alkyl, aryl, or aryl-$C_1-C_6$ alkyl-; and
$OY^1$ and $OY^2$ are independently selected from:
  b) $C_1-C_8$ alkoxy, and
when taken together with B, $OY^1$ and $OY^2$ form:
  c) a cyclic boronic ester where said cyclic boronic ester contains from 2 to 20 carbon atoms, and, optionally, 1, 2, or 3 heteroatoms which can be N, S, or O;
said process comprising:
(1) (addition) contacting a compound of Formula (I):

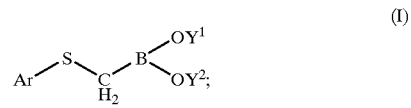

(I)

wherein Ar is aryl;
with a hindered base followed by addition of a hydrocarbon containing an electrophilic center selected from:
  L—$CH_2(CH_2)_mW$,
  L—$CH_2(C=O)R^5$,
  $CH_2=CH_2(C=O)R^5$,
  L—$CHR^4(CR^{4a}R^3)_mW$,
  L—$CHR^{4a}(C=O)R^5$,
  $CHR^4=CHR^{4a}(C=O)R^5$,
  L—$CHR^{4a}(P=O)(OR^6)_2$,
  $CHR^4=CHR^{4a}(P=O)(OR^6)_2$,
  L—$CHR^{4a}SO_2NH_2$,
  $CHR^4=CHR^{4a}SO_2NH_2$, L—CHR$^{4a}$SO$_3$R$^6$,
CHR$^4$=CHR$^{4a}$SO$_3$R$^6$;

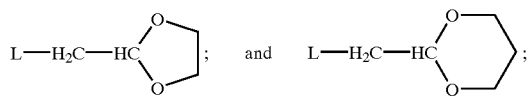

to form a compound of Formula (II):

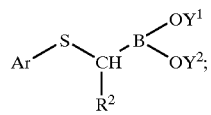
(II)

wherein L is a leaving group;

(2) (alkylation) contacting the compound of Formula (II) with an alkylating agent to form a compound of Formula is (III):

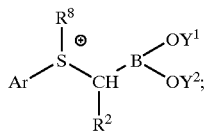
(III)

wherein R$^8$ is C$_1$–C$_6$ alkyl;

(3) (halogenation) contacting the compound of Formula (III) with a metal halide M—X to form a compound of Formula (IV):

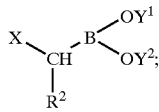
(IV)

wherein X is halogen; M is an alkali metal or an alkaline-earth metal; and (4) (amination) aminating the compound of Formula (IV) by either
 (i) contacting the compound of Formula (IV) with NaN$_3$ followed by addition of a hydrogenation agent to form the compound of Formula (V); or
 (ii) contacting the compound of Formula (IV) wherein R$^2$ is —CH$_2$(CH$_2$)$_m$W or —CHR$^4$(CR$^{4a}$R$^3$)$_m$W; with lithium hexamethyldisilazane followed addition of a strong acid; to form the compound of Formula (V);

or alternatively, Step (2) may be followed by (5) (direct amination) aminating the compound of Formula (III) by either
 (i) contacting the compound of Formula (III) with NaN$_3$ followed by addition of a hydrogenation agent to form the compound of Formula (V); or
 (ii) contacting the compound of Formula (III) wherein R$^2$ is —CH$_2$(CH$_2$)$_m$W or —CHR$^4$(CR$^{4a}$R$^3$)$_m$W; with lithium hexamethyldisilazane followed addition of a strong acid; to form the compound of Formula (V).

DETAILED DESCRIPTION OF THE INVENTION

In a first embodiment, the present invention provides a novel process for the preparation of compounds of formula (V):

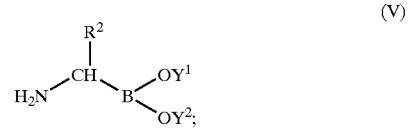
(V)

wherein:

R$^2$ is —CH$_2$(CH$_2$)$_m$W, —CH$_2$(C=O)R$^5$, —CH$_2$CH$_2$(C=O)R$^5$, —CHR$^4$(CR$^{4a}$R$^3$)$_m$W, —CHR$^{4a}$(C=O)R$^5$, —CHR$^4$CHR$^{4a}$(C=O)R$^5$, —CHR$^{4a}$(P=O) (OR$^6$)$_2$, —CHR$^4$CHR$^{4a}$(P=O) (OR$^6$)$_2$, —CHR$^{4a}$SO$_2$NH$_2$, —CHR$^4$CHR$^{4a}$SO$_2$NH$_2$, —CHR$^{4a}$SO$_3$R$^6$, —CHR$^4$CHR$^{4a}$SO$_3$R$^6$;

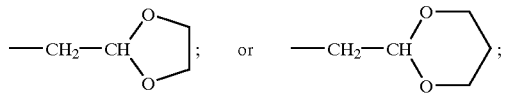

R$^3$ is H, F, Cl or Br;
m is 0–4;
W is —CH$_2$F, —CHF$_2$, —CF$_3$, —CH$_2$Cl, —CHC$_{l2}$, or —CCl$_3$;
R$^4$ and R$^{4a}$ are independently H or C$_1$–C$_6$ alkyl, aryl, or aryl-C$_1$–C$_6$ alkyl-;
R$^5$ is C$_1$–C$_6$ alkyl, aryl, aryl-C$_1$–C$_6$ alkyl-, —OR$^6$, —NH$_2$, —N(R$^6$)$_2$, or —NHR$^6$;
R$^6$ is C$_1$–C$_6$ alkyl, aryl, or aryl-C$_1$–C$_6$ alkyl-; and
OY$^1$ and OY$^2$ are independently selected from:
 b) C$_1$–C$_8$ alkoxy, and
when taken together with B, OY$^1$ and OY$^2$ form:
 c) a cyclic boronic ester where said cyclic boronic ester contains from 2 to 20 carbon atoms, and, optionally, 1, 2, or 3 heteroatoms which can be N, S, or O;
said process comprising:
(1) contacting a compound of Formula (I):

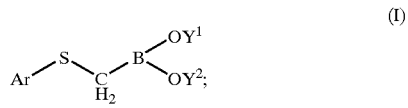
(I)

wherein Ar is aryl;
with a hindered base followed by addition of a hydrocarbon containing an electrophilic center selected from:
 L—CH$_2$(CH$_2$)$_m$W,
 L—CH$_2$(C=O)R$^5$,
 CH$_2$=CH$_2$(C=O)R$^5$,
 L—CHR$^4$(CR$^{4a}$R$^3$)$_m$W,
 L—CHR$^{4a}$(C=O)R$^5$,
 CHR$^4$=CHR$^{4a}$(C=O)R$^5$,
 L—CHR$^{4a}$(P=O)(ORg$^6$)$_2$,
 CHR$^4$=CHR$^{4a}$(P=O)(OR$^6$)$_2$,
 L- CHR$^{4a}$SO$_2$NH$_2$,
 CHR$^4$=CHR$^{4a}$SO$_2$NH$_2$, L—CHR$^{4a}$SO$_3$R$^6$,
CHR$^4$=CHR$^{4a}$SO$_3$R$^6$;

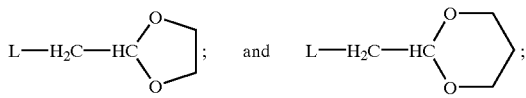

to form a compound of Formula (II):

(II)

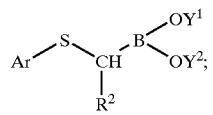

wherein L is a leaving group;
(2) contacting the compound of Formula (II) with an alkylating agent to form a compound of Formula (III):

(III)

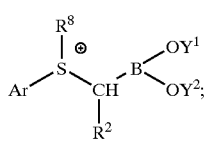

wherein R$^8$ is C$_1$–C$_6$ alkyl;
(3) contacting the compound of Formula (III) with a metal halide M—X to form a compound of Formula (IV):

(IV)

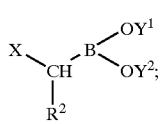

wherein X is halogen; M is an alkali metal or an alkaline-earth metal; and
(4) aminating the compound of Formula (IV) by either
  (i) contacting the compound of Formula (IV) with NaN$_3$ followed by addition of a hydrogenation agent to form the compound of Formula (V); or
  (ii) contacting the compound of Formula (IV) wherein R$^2$ is —CH$_2$(CH$_2$)$_m$W or —CHR$^4$(CR$^{4a}$R$^3$)$_m$W; with lithium hexamethyldisilazane followed addition of a strong acid; to form the compound of Formula (V);
or alternatively, Step (2) may be followed by
(5) aminating the compound of Formula (III) by either
  (i) contacting the compound of Formula (III) with NaN$_3$ followed by addition of a hydrogenation agent to form the compound of Formula (V); or
  (ii) contacting the compound of Formula (III) wherein R$^2$ is —CH$_2$(CH$_2$)$_m$W or —CHR$^4$(CR$^{4a}$R$^3$)$_m$W; with lithium hexamethyldisilazane followed addition of a strong acid; to form the compound of Formula (V).

In another embodiment the present invention provides a process for the preparation of a compound of Formula (V) wherein:
R$^2$ is —CH$_2$(CH$_2$)$_m$W, —CH$_2$(C=O)R$^5$, or —CH$_2$CH$_2$(C=O)R$^5$;
m is 0–2;
W is —CH$_2$F, —CHF$_2$, —CF$_3$, —CH$_2$Cl, —CHC$_2$, or —CCl$_3$;

R$^5$ is C$_1$–C$_6$ alkyl, aryl, aryl-C$_1$–C$_6$ alkyl-, —OR$^6$, —NH$_2$, —N(R$^6$)$_2$, or —NHR$^6$;
R$^6$ is C$_1$–C$_6$ alkyl, aryl, or aryl-C$_1$–C$_6$ alkyl-; and
OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;
said process comprising:
(1) contacting a compound of Formula (I):

(I)

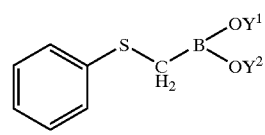

with a hindered base followed by a hydrocarbon containing an electrophilic center selected from:
L—CH$_2$(CH$_2$)$_m$W,
L—CH$_2$(C=O)R$^5$, and
CH$_2$=CH$_2$(C=O)R$^5$;
to form a compound of Formula (II):

(II)

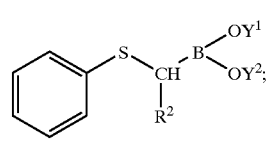

wherein L is a leaving group selected from:
I, Br, Cl, methylsulfonyloxy, p-toluylsulfonyloxy and trifluoromethylsulfonyloxy;
(2) contacting the compound of Formula (II) with an alkylating agent to form a compound of Formula (III):

(III)

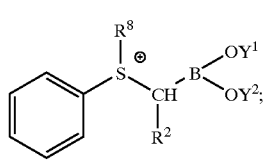

wherein R$^8$ is C$_1$–C$_6$ alkyl;
(3) contacting the compound of Formula (III) with a metal halide M—X to form a compound of Formula (IV):

(IV)

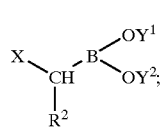

wherein X is halogen; M is a alkali metal or an alkaline-earth metal; and
(4) aminating the compound of Formula (IV) by either
  (i) contacting the compound of Formula (IV) with NaN$_3$ followed by addition of a hydrogenation agent to form the compound of Formula (V); or
  (ii) contacting the compound of Formula (IV) wherein R$^2$ is —CH$_2$(CH$_2$)$_m$W; with lithium hexamethyldisilazane followed addition of a strong acid; to form the compound of Formula (V);

or alternatively, Step (2) may be followed by (5) aminating the compound of Formula (III) by either
  (i) contacting the compound of Formula (III) with NaN$_3$ followed by addition of a hydrogenation agent to form the compound of Formula (V); or
  (ii) contacting the compound of Formula (III) wherein R$^2$ is —CH$_2$(CH$_2$)$_m$W; with lithium hexamethyldisilazane followed addition of a strong acid; to form the compound of Formula (V).

In another alternative embodiment, the present invention provides provide a process for the preparation of a compound of Formula (V) wherein:

R$^2$ is —CH$_2$(CH$_2$)$_m$W, —CH$_2$(C=O)OR$^6$, or —CH$_2$CH$_2$(C=O)OR$^6$;

m is 0–2;

W is —CH$_2$F, —CHF$_2$, —CF$_3$, —CH$_2$Cl, —CHC$_{12}$, or —CCl$_3$;

R$^6$ is C$_1$–C$_6$ alkyl, aryl, or aryl-C$_1$–C$_6$ alkyl-; and

OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

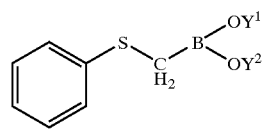

(I)

with a hindered base selected from:
lithium diisopropylamide, lithium 2,2,6,6-tetramethylpiperidine, lithium hexamethyldisilazane and n-butyllithium;

followed by a hydrocarbon containing an electrophilic center selected from:
L—CH$_2$(CH$_2$)$_m$W,
L—CH$_2$(C=O)OR$^6$, and
CH$_2$=CH$_2$(C=O)OR$^6$;

to form a compound of Formula (II):

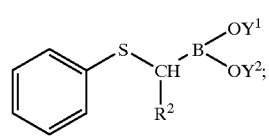

(II)

wherein L is a leaving group selected from:
I, Br, Cl, methylsulfonyloxy, p-toluylsulfonyloxy and trifluoromethylsulfonyloxy;

(2) contacting the compound of Formula (II) with an alkylating agent selected from:
C$_1$–C$_6$ alkyl halides, trimethyloxonium tetrafluoroborate, dimethylsulfate and methyltriflate;

to form a compound of Formula (III):

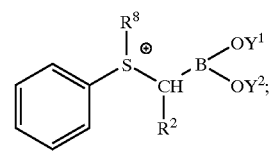

(III)

wherein R$^8$ is C$_1$–C$_6$ alkyl;

(3) contacting the compound of Formula (III) with a metal halide M—X selected from sodium iodide, lithium bromide and potassium iodide;

to form a compound of Formula (IV):

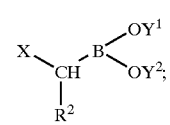

(IV)

wherein X is I or Br; and (4) aminating the compound of Formula (IV) by either
  (i) contacting the compound of Formula (IV) with NaN$_3$ followed by contacting a hydrogenation agent selected from:
    H$_2$/Pd—C; and
    SnCl$_2$ in methanol;
  to form the compound of Formula (V); or
  (ii) contacting the compound of Formula (IV) wherein R$^2$ is —CH$_2$(CH$_2$)$_m$W lithium hexamethyldisilazane followed by contacting a strong acid selected from:
    anhydrous HCl; and
    trifluoroacetic acid;
  to form the compound of Formula (V).

In an alternative embodiment, the present invention provides a process for the preparation of a compound of Formula (V) wherein:

R$^2$ is —CH$_2$(CH$_2$)$_m$W, —CH$_2$(C=O)OR$^6$, or —CH$_2$CH$_2$(C=O)OR$^6$;

m is 0–2;

W is —CH$_2$F, —CHF$_2$, —CF$_3$, —CH$_2$Cl, —CHCl$_2$, or —CCl$_3$;

R$^6$ is C$_1$–C$_6$ alkyl, aryl, or aryl-C$_{1-6}$ alkyl-; and

OY$^1$ and OY$^2$ are taken together with B to form a cyclic boronic ester where said cyclic boronic ester is formed from the group: pinanediol and pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

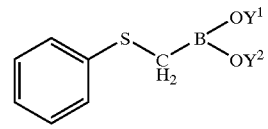

(I)

with a hindered base selected from:
lithium diisopropylamide, lithium 2,2,6,6-tetramethylpiperidine and lithium hexamethyldisilazane;

followed by a hydrocarbon containing an electrophilic center selected from:
L—CH$_2$(CH$_2$)$_m$W,
L—CH$_2$(C=O)OR$^6$, and
CH$_2$=CH$_2$(C=O)OR$^6$;
to form a compound of Formula (II):

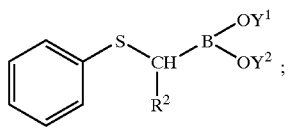

(II)

wherein L is I or Br;

(2) contacting the compound of Formula (II) with an alkylating agent selected from:
methyl iodide, ethyl iodide and trimethyloxonium tetrafluoroborate;
to form a compound of Formula (III):

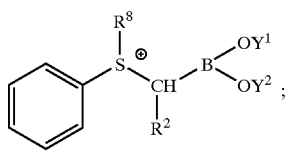

(III)

wherein R$^8$ is methyl or ethyl;

(3) contacting the compound of Formula (III) with sodium iodide to form a compound of Formula (IV):

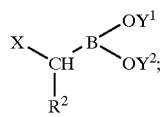

(IV)

wherein X is I; and (4) aminating the compound of Formula (IV) by either
(i) contacting the compound of Formula (IV) with NaN$_3$ followed by addition of H$_2$/Pd—C to form the compound of Formula (V); or
(ii) contacting the compound of Formula (IV) when R$^2$ is —CH$_2$(CH$_2$)$_m$W; with lithium hexamethyldisilazane followed addition of a strong acid selected from:
anhydrous HCl; and
trifluoroacetic acid;
to form the compound of Formula (V).

In another alternative embodiment, the present invention provides a process for the preparation of a compound of Formula (V-1):

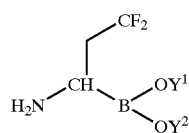

(V-1)

wherein OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:
(1) contacting a compound of Formula (I):

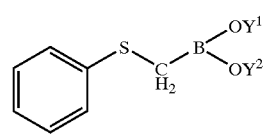

(I)

with a hindered base followed by L—CH$_2$CHF$_2$;
to form a compound of Formula (II-1):

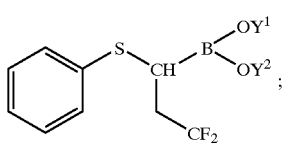

(II-1)

wherein L is a leaving group;

(2) contacting the compound of Formula (II-1) with an alkylating agent to form a compound of Formula (III-1):

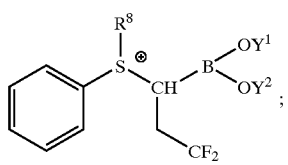

(III-1)

wherein R$^8$ is C$_1$–C$_6$ alkyl;

(3) contacting the compound of Formula (III-1) with a metal halide M—X to form a compound of Formula (IV-1):

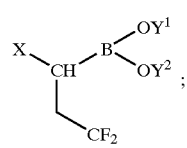

(IV-i)

wherein X is halogen; M is a alkali metal or an alkaline-earth metal; and (4) aminating the compound of Formula (IV-1) by either
(i) contacting the compound of Formula (IV-1) with NaN$_3$ followed by addition of a hydrogenation agent to form the compound of Formula (V-1); or
(ii) contacting the compound of Formula (IV-1) with lithium hexamethyldisilazane followed addition of a strong acid; to form the compound of Formula (V-1);

or alternatively, Step (2) may be followed by (5) aminating the compound of Formula (III-1) by either
(i) contacting the compound of Formula (III-1) with NaN$_3$ followed by addition of a hydrogenation agent to form the compound of Formula (V-1); or
(ii) contacting the compound of Formula (III-1) with lithium hexamethyldisilazane followed addition of a strong acid; to form the compound of Formula (V-1).

In another alternative embodiment, the present invention provides a process for the preparation of a compound of Formula (V-1) wherein:
OY$^1$ and OY$^2$ are taken together with B to form a cyclic boronic ester where said cyclic boronic ester is formed from the group: pinanediol and pinacol;
said process comprising:
(1) contacting a compound of Formula (I):

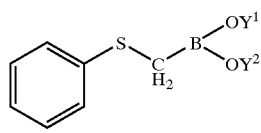
(I)

with a hindered base selected from:
lithium diisopropylamide, lithium 2,2,6,6-tetramethylpiperidine, lithium hexamethyldisilazane and n-butyllithium;
followed by L—CH$_2$CHF$_2$;
to form a compound of Formula (II-1):

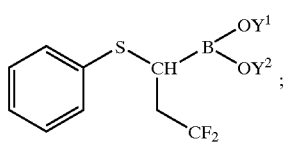
(II-1)

wherein L is a leaving group selected from:
I, Br, Cl, methylsulfonyloxy, p-toluylsulfonyloxy and trifluoromethylsulfonyloxy;
(2) contacting the compound of Formula (II-1) with an alkylating agent selected from:
C$_1$–C$_6$ alkyl halides, trimethyloxonium tetrafluoroborate, dimethylsulfate and methyltriflate;
to form a compound of Formula (III-1):

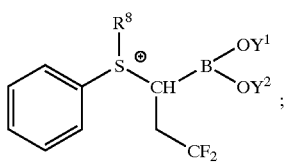
(III-1)

wherein R$^8$ is C$_1$—C$_6$ alkyl;
(3) contacting the compound of Formula (III-1) with a metal halide M—X selected from sodium iodide, lithium bromide and potassium iodide;
to form a compound of Formula (IV-1):

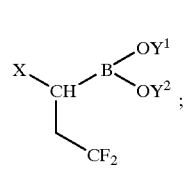
(IV-i)

wherein X is I or Br; and
(4) aminating the compound of Formula (IV-1) by either
 (i) contacting the compound of Formula (IV-1) with NaN$_3$ followed by addition of a hydrogenation agent selected from:

H$_2$/Pd—C; and
SnCl$_2$ in methanol;
to form the compound of Formula (V-1); or
(ii) contacting the compound of Formula (IV-1) with lithium hexamethyldisilazane followed addition of a strong acid a strong acid selected from:
anhydrous HCl; and
trifluoroacetic acid;
to form the compound of Formula (V-1).
In another alternative embodiment, the process for the preparation of a compound of Formula (V-1) comprises:
(1) contacting a compound of Formula (I):

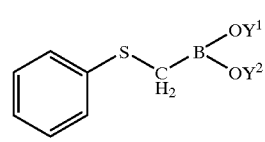
(I)

with a hindered base selected from:
lithium diisopropylamide, lithium 2,2,6,6-tetramethylpiperidine and lithium hexamethyldisilazane;
followed by L—CH$_2$CHF$_2$;
to form a compound of Formula (II-1):

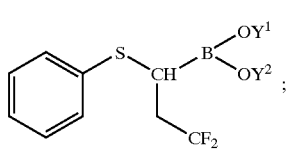
(II-1)

wherein L is I or Br;
(2) contacting the compound of Formula (II-1) with an alkylating agent selected from:
methyl iodide, ethyl iodide and trimethyloxonium tetrafluoroborate;
to form a compound of Formula (III-1):

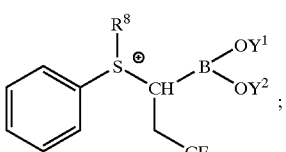
(III-1)

wherein R$^8$ is methyl or ethyl;
(3) contacting the compound of Formula (III-1) with sodium iodide to form a compound of Formula (IV-1):

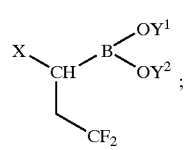
(IV-i)

wherein X is I; and
(4) aminating the compound of Formula (IV-1) by either
 (i) contacting the compound of Formula (IV-1) with NaN$_3$ followed by addition of H$_2$/Pd—C to form the compound of Formula (V-1); or (ii) contacting the compound of Formula (IV-1) with lithium hexamethyldisilazane followed addition of a strong acid a strong acid selected from:
anhydrous HCl; and
trifluoroacetic acid;
to form the compound of Formula (V-1).

In another alternative embodiment, the present invention provides a process for the preparation of a compound of Formula (V-2):

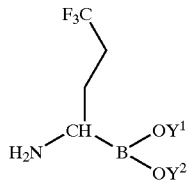

(V-2)

wherein
OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;
said process comprising:
(1) contacting a compound of Formula (I):

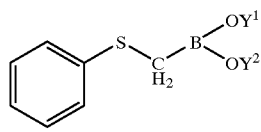

(I)

with a hindered base followed by L—CH$_2$CH$_2$CF$_3$;
to form a compound of Formula (II-2):

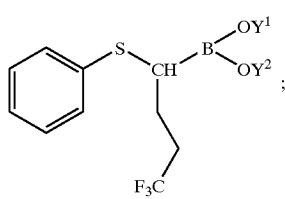

(II-2)

wherein L is a leaving group;
(2) contacting the compound of Formula (II-2) with an alkylating agent to form a compound of Formula (III-2):

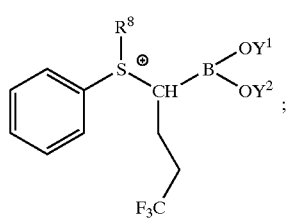

(III-2)

wherein R$^8$ is C$_1$–C$_6$ alkyl;

(3) contacting the compound of Formula (III-2) with a metal halide M—X to form a compound of Formula (IV-2):

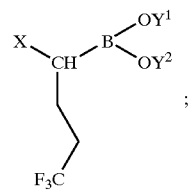

(IV-2)

wherein X is halogen; M is a alkali metal or an alkaline-earth metal; and
(4) aminating the compound of Formula (IV-2) by either
(ii) contacting the compound of Formula (IV-2) with NaN$_3$ followed by addition of a hydrogenation agent to form the compound of Formula (V-2); or
(ii) contacting the compound of Formula (IV-2) with lithium hexamethyldisilazane followed addition of a strong acid; to form the compound of Formula (V-2);
or alternatively, Step (2) may be followed by
(5) aminating the compound of Formula (III-2) by either
(i) contacting the compound of Formula (III-2) with NaN$_3$ followed by addition of a hydrogenation agent to form the compound of Formula (V-2); or
(ii) contacting the compound of Formula (III-2) with lithium hexamethyldisilazane followed addition of a strong acid; to form the compound of Formula (V-2).

In another alternative embodiment, the present invention provides a process for the preparation of a compound of Formula (V-2) wherein:
OY$^1$ and OY$^2$ are taken together with B to form a cyclic boronic ester where said cyclic boronic ester is formed from the group: pinanediol and pinacol;
said process comprising:
(1) contacting a compound of Formula (I):

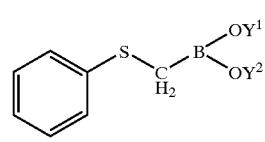

(I)

with a hindered base selected from:
lithium diisopropylamide, lithium 2,2,6,6-tetramethylpiperidine, lithium hexamethyldisilazane and n-butyllithium;
followed by L—CH$_2$CH$_2$CF$_3$;
to form a compound of Formula (II-2):

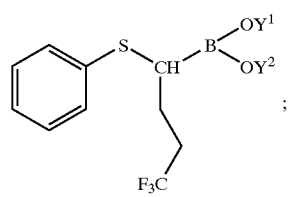

(II-2)

L is a leaving group selected from:
I, Br, Cl, methylsulfonyloxy, p-toluylsulfonyloxy and trifluoromethylsulfonyloxy;

(2) contacting the compound of Formula (II-2) with an alkylating agent selected from:
C$_1$–C$_6$ alkyl halides, trimethyloxonium tetrafluoroborate, dimethylsulfate and methyltriflate;
to form a compound of Formula (III-2):

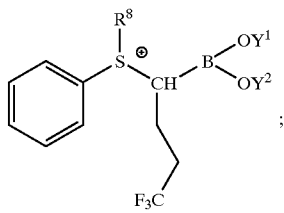

(III-2)

wherein R$^8$ is C$_1$–C$_6$ alkyl;

(3) contacting the compound of Formula (III-2) with a metal halide M—X selected from sodium iodide, lithium bromide and potassium iodide;
to form a compound of Formula (IV-2):

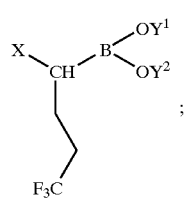

(IV-2)

wherein X is I or Br; and (4) aminating the compound of Formula (IV-2) by either
   (i) contacting the compound of Formula (IV-2) with NaN$_3$ followed by addition of a hydrogenation agent selected from:
   H$_2$/Pd—C; and
   SnCl$_2$ in methanol;
   to form the compound of Formula (V-2); or
   (ii) contacting the compound of Formula (IV-2) with lithium hexamethyldisilazane followed addition of a strong acid a strong acid selected from:
   anhydrous HCl; and
   trifluoroacetic acid;
   to form the compound of Formula (V-2).

In another alternative embodiment, the process for the preparation of a compound of Formula (V-2) comprises:

(1) contacting a compound of Formula (I):

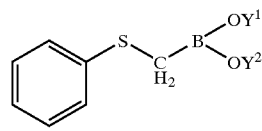

(I)

with a hindered base selected from:
lithium diisopropylamide, lithium 2,2,6,6-tetramethylpiperidine and lithium hexamethyldisilazane;
followed by L—CH$_2$CH$_2$CF$_3$;
to form a compound of Formula (II-2):

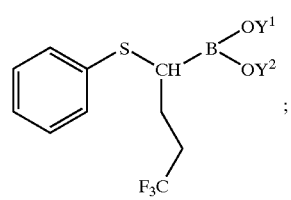

(II-2)

wherein L is I or Br;

(2) contacting the compound of Formula (II-2) with an alkylating agent selected from:
methyl iodide, ethyl iodide and trimethyloxonium tetrafluoroborate;
to form a compound of Formula (III-2):

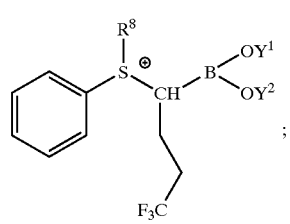

(III-i)

wherein R$^8$ is methyl or ethyl;

(3) contacting the compound of Formula (III-2) with sodium iodide to form a compound of Formula (IV-2):

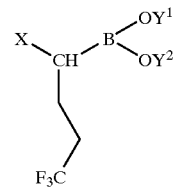

(IV-2)

wherein X is I; and (4) aminating the compound of Formula (IV-2) by either
   (i) contacting the compound of Formula (IV-2) with NaN$_3$ followed by addition of H$_2$/Pd—C to form the compound of Formula (V-2); or
   (ii) contacting the compound of Formula (IV-2) with lithium hexamethyldisilazane followed addition of a strong acid a strong acid selected from:
   anhydrous HCl; and
   trifluoroacetic acid;
   to form the compound of Formula (V-2).

In another alternative embodiment, the present invention provides a process for the preparation of a compound of Formula (V-3):

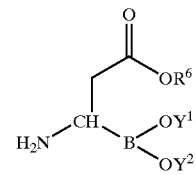

(V-3)

wherein
R⁶ is Me or t-Bu; and
OY¹ and OY² are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;
said process comprising:
(1) contacting a compound of Formula (I):

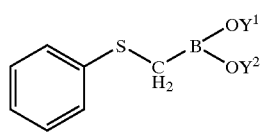
(I)

with a hindered base followed by L—CH₂C(=O)OR⁶;
to form a compound of Formula (II-3):

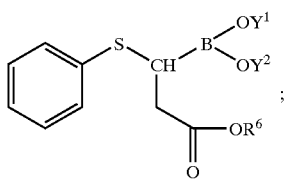
(II-3)

wherein L is a leaving group;
(2) contacting the compound of Formula (II-3) with an alkylating agent to form a compound of Formula (III-3):

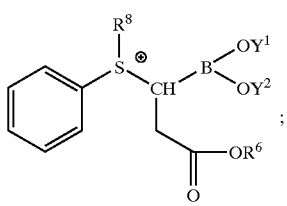
(III-3)

wherein R⁸ is C₁–C₆ alkyl;
(3) contacting the compound of Formula (III-3) with a metal halide M—X to form a compound of Formula (IV-3):

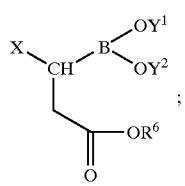
(IV-3)

wherein X is halogen; M is a alkali metal or an alkaline-earth metal; and
(4) aminating the compound of Formula (IV-3) by contacting the compound of Formula (IV-3) with NaN₃ followed by addition of a hydrogenation agent to form the compound of Formula (V-3); or
or alternatively, Step (2) may be followed by
(5) aminating the compound of Formula (III-3) by contacting the compound of Formula (III-3) with NaN₃ followed by addition of a hydrogenation agent to form the compound of Formula (V-3).

In another alternative embodiment, the present invention provides a process for the preparation of a compound of Formula (V-3) wherein:
R⁶ is Me or t-Bu; and
OY¹ and OY² are taken together with B to form a cyclic boronic ester where said cyclic boronic ester is formed from the group: pinanediol and pinacol;
said process comprising:
(1) contacting a compound of Formula (I):

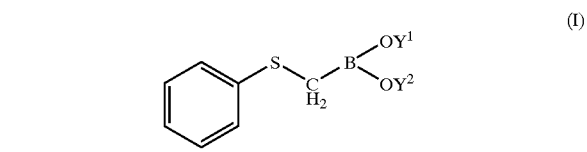
(I)

with a hindered base selected from:
lithium diisopropylamide, lithium 2,2,6,6-tetramethylpiperidine, lithium hexamethyldisilazane and n-butyllithium;
followed by L—CH₂C(=O)OR⁶;
to form a compound of Formula (II-3):

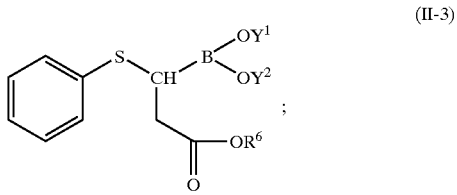
(II-3)

wherein L is a leaving group selected from:
I, Br, Cl, methylsulfonyloxy, p-toluylsulfonyloxy and trifluoromethylsulfonyloxy;
(2) contacting the compound of Formula (II-3) with an alkylating agent selected from:
C₁–C₆ alkyl halides, trimethyloxonium tetrafluoroborate, dimethylsulfate and methyltriflate;
to form a compound of Formula (III-3):

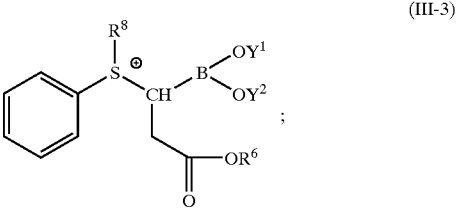
(III-3)

wherein R⁸ is C₁–C₆ alkyl;
(3) contacting the compound of Formula (III-3) with a metal halide M—X selected from sodium iodide, lithium bromide and potassium iodide;
to form a compound of Formula (IV-3):

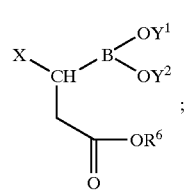
(IV-3)

wherein X is I or Br; and (4) aminating the compound of Formula (IV-3) by contacting the compound of Formula (IV-3) with NaN$_3$ followed by addition of a hydrogenation agent selected from:
H$_2$/Pd—C; and
SnCl$_2$ in methanol;
to form the compound of Formula (V-3).

In another alternative embodiment, the process for the preparation of a compound of Formula (V-3) comprises:

(1) contacting a compound of Formula (I):

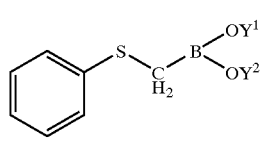

(I)

with a hindered base selected from:
lithium diisopropylamide, lithium 2,2,6,6-tetramethylpiperidine and lithium hexamethyldisilazane;
followed by L—CH$_2$C(=O)OR$^6$;
to form a compound of Formula (II-3):

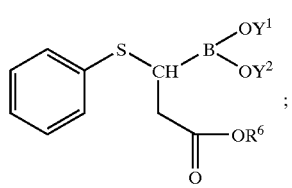

(II-3)

wherein L is I or Br;

(2) contacting the compound of Formula (II-3) with an alkylating agent selected from:
methyl iodide, ethyl iodide and trimethyloxonium tetrafluoroborate;
to form a compound of Formula (III-3):

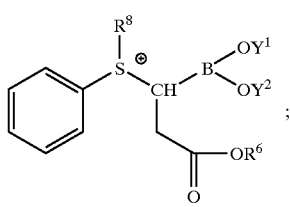

(III-3)

wherein R$^8$ is methyl or ethyl;

(3) contacting the compound of Formula (III-3) with sodium iodide to form a compound of Formula (IV-3):

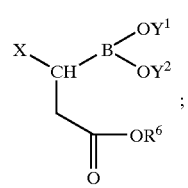

(IV-3)

wherein X is I; and (4) aminating the compound of Formula (IV-3) by contacting the compound of Formula (IV-3) with NaN$_3$ followed by addition of H$_2$/Pd—C to form the compound of Formula (V-3).

In another alternative embodiment, the present invention provides a process for the preparation of a compound of Formula (V-4):

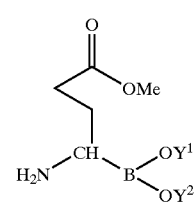

(V-4)

wherein

OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

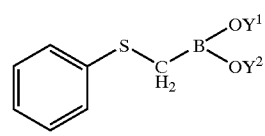

(I)

with a hindered base followed CH$_2$=CH(C=O)OMe;
to form a compound of Formula (II-4):

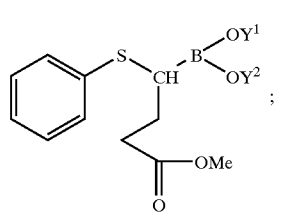

(II-4)

(2) contacting the compound of Formula (II-4) with an alkylating agent to form a compound of Formula (III-4):

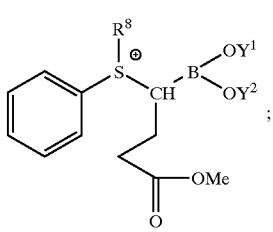

(III-4)

wherein R$^8$ is C$_1$–C$_6$ alkyl;

(3) contacting the compound of Formula (III-4) with a metal halide M—X to form a compound of Formula (IV-4):

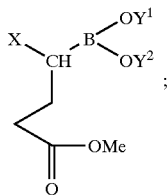

(IV-4)

wherein X is halogen; M is a alkali metal or an alkaline-earth metal; and (4) aminating the compound of Formula (IV-4) by contacting the compound of Formula (IV-4) with NaN$_3$ followed by addition of a hydrogenation agent to form the compound of Formula (V-4); or or alternatively, Step (2) may be followed by (5) aminating the compound of Formula (III-4) by contacting the compound of Formula (III-4) with NaN$_3$ followed by addition of a hydrogenation agent to form the compound of Formula (V-4).

In another alternative embodiment, the present invention provides a process for the preparation of a compound of Formula (V-4) wherein:

OY$^1$ and OY$^2$ are taken together with B to form a cyclic boronic ester where said cyclic boronic ester is formed from the group: pinanediol and pinacol;

said process comprising:

(1) contacting a compound of Formula (I):

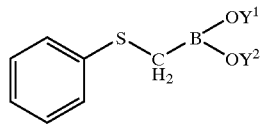

(I)

with a hindered base selected from:
lithium diisopropylamide, lithium 2,2,6,6-tetramethylpiperidine, lithium hexamethyldisilazane and n-butyllithium;
followed by by CH$_2$=CH(=O)OMe;
to form a compound of Formula (II-4):

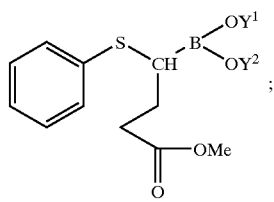

(II-4)

(2) contacting the compound of Formula (II-4) with an alkylating agent selected from:
C$_1$-C$_6$ alkyl halides, trimethyloxonium tetrafluoroborate, dimethylsulfate and methyltriflate;

to form a compound of Formula (III-4):

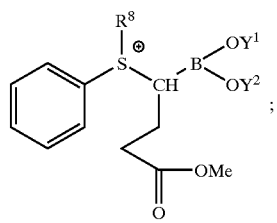

(III-4)

wherein R$^8$ is C$_1$-C$_6$ alkyl;

(3) contacting the compound of Formula (III-4) with a metal halide M—X selected from sodium iodide, lithium bromide and potassium iodide;

to form a compound of Formula (IV-4):

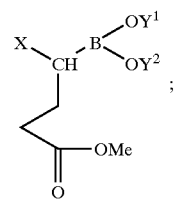

(IV-4)

wherein X is I or Br; and (4) aminating the compound of Formula (IV-4) by contacting the compound of Formula (IV-4) with NaN$_3$ followed by addition of a hydrogenation agent selected from:
H$_2$/Pd—C; and
SnCl$_2$ in methanol;
to form the compound of Formula (V-4).

In another alternative embodiment, the process for the preparation of a compound of Formula (V-4) comprises:

(1) contacting a compound of Formula (I):

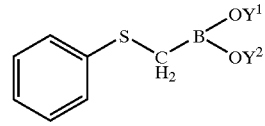

(I)

with a hindered base selected from:
lithium diisopropylamide, lithium 2,2,6,6-tetramethylpiperidine and lithium hexamethyldisilazane;
followed by CH$_2$=CH(=O)OMe;
L is I or Br;
to form a compound of Formula (II-4):

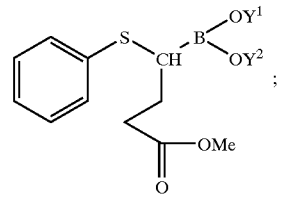

(II-4)

(2) contacting the compound of Formula (II-4) with an alkylating agent selected from:
methyl iodide, ethyl iodide and trimethyloxonium tetrafluoroborate;
to form a compound of Formula (III-4):

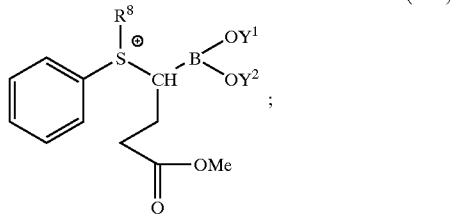

wherein $R^8$ is methyl or ethyl;

(3) contacting the compound of Formula (III-4) with sodium iodide to form a compound of Formula (IV-4):

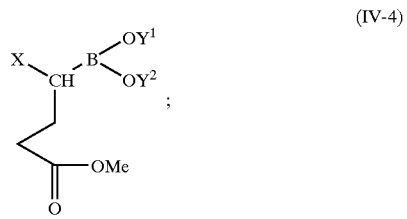

wherein X is I; and (4) aminating the compound of Formula (IV-4) by contacting the compound of Formula (IV-4) with $NaN_3$ followed by addition of $H_2/Pd$—C to form the compound of Formula (V-4).

The present invention also provides compounds of Formula (V-a):

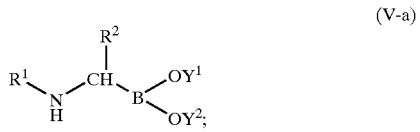

wherein:
$R^1$ is H or $C_1$–$C_6$ alkyl;
$R^2$ is —$CH_2(CH_2)_m W$, —$CH_2(C=O)R^5$, —$CH_2CH_2(C=O)R^5$, —$CHR^4(CR^{4a}R^3)_m W$, —$CHR^{4a}(C=O)R^5$, —$CHR^4CHR^{4a}(C=O)R^5$, —$CHR^{4a}(P=O)(OR^6)_2$, —$CHR^4CHR^{4a}(P=O)(OR^6)_2$, —$CHR^{4a}SO_2NH_2$, —$CHR^4CHR^{4a}SO_2NH_2$, —$CHR^{4a}SO_3R^6$, —$CHR^4CHR^{4a}SO_3R^6$;

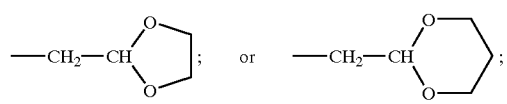

$R^3$ is H, F, Cl or Br;
m is 0–4;
W is —$CH_2F$, —$CHF_2$, —$CF_3$, —$CHCl_2$, or —$CCl_3$;
$R^4$ and $R^{4a}$ are independently H or $C_1$–$C_6$ alkyl, aryl, or aryl-$C_1$–$C_6$ alkyl-;
$R^5$ is $C_1$–$C_6$ alkyl, aryl, aryl-$C_1$–$C_6$ alkyl-, —$OR^6$, —$NH_2$, —$N(R^6)_2$, or —$NHR^6$;

$R^6$ is H, $C_1$–$C_6$ alkyl, aryl, or aryl-$C_1$–$C_6$ alkyl-; and
$OY^1$ and $OY^2$ are independently selected from:
b) $C_1$–$C_8$ alkoxy, and
when taken together with B, $OY^1$ and $OY^2$ form:
c) a cyclic boronic ester where said cyclic boronic ester contains from 2 to 20 carbon atoms, and, optionally, 1, 2, or 3 heteroatoms which can be N, S, or O.

In another embodiment the present invention provides compounds of Formula (V-a) wherein:
$R^1$ is H or $C_1$–$C_6$ alkyl;
$R^2$ is —$CH_2CHF_2$, —$CH_2CH_2CF_3$, —$CH_2(C=O)R^5$, or —$CH_2CH_2$—$(C=O)R^5$;
$R^5$ is $C_1$–$C_6$ alkyl, aryl, aryl-$C_1$–$C_6$ alkyl-, —$OR^6$, or —$N(R^6)_2$;
$R^6$ is H, $C_1$–$C_6$ alkyl, aryl, or aryl-$C_1$–$C_6$ alkyl-; and
$OY^1$ and $OY^2$ are independently selected from:
a) —OH,
b) $C_1$–$C_8$ alkoxy, and
when taken together with B, $OY^1$ and $OY^2$ form:
c) a cyclic boronic ester where said cyclic boronic ester contains from 2 to 14 carbon atoms, and, optionally, 1, 2, or 3 heteroatoms which can be N, S, or O.

In another alternative embodiment, the present invention provides compounds of Formula (V-a) wherein:
$R^1$ is H;
$R^2$ is —$CH_2CHF_2$, —$CH_2CH_2CF_3$, —$CH_2(C=O)OR^6$, or —$CH_2CH_2$—$(C=O)OR^6$;
$R^6$ is H or $C_1$–$C_6$ alkyl; and
$OY^1$ and $OY^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol.

In another alternative embodiment, the present invention provides a compound selected from:
1-amino-3,3-difluoropropyl boronate pinacol ester;
1-amino-4,4,4-trifluorobutyl boronate pinanediol ester;
1-amino-2-t-butoxycarbonylethane-1-boronate pinanediol ester;
1-amino-2-methoxycarbonylethane-1-boronate pinanediol ester;
1-amino-2-hydroxycarbonylethane-1-boronate pinanediol ester;
1-amino-3-methoxycarbonyl-propane-1-boronate pinanediol ester; and
1-amino-3-hydroxycarbonyl-propane-1-boronate pinanediol ester.

The following terms and abbreviations are used herein and defined as follows. The abbreviation:
"THF" as used herein means tetrahydrofuran,
"THF" as used herein means tetrahydrofuran,
"DMSO" as used herein means dimethylsulfoxide,
"DMF" as used herein means N,N-dimethylformamide,
"BuLi" as used herein means butyllithium,
"NaH" as used herein means sodium hydride,
"LDA" as used herein means lithium diisopropylamide,
"HMPA" as used herein means hexamethyphosphoric triamide,
"TMEDA" as used herein means N,N,N',N',-tetramethylethylenediamine.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable ether solvents include: tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable basic solvents include: 2-, 3-, or 4-picoline, pyrrole, pyrrolidine, morpholine, pyridine, or piperidine.

Suitable hydrocarbon solvents include: benzene, cyclohexane, pentane, hexane, toluene, cycloheptane, methylcyclohexane, heptane, ethylbenzene, m-, o-, or p-xylene, octane, indane, nonane, or naphthalene. As used herein, the term "hydrocarbon containing an electrophilic center" or "electrophile" refers to any electrophilic group which selectively reacts with a phenylthio boronate of Formula (I) to form a compound of Formula (II). Examples of hydrocarbons containing an electrophilic center include, but are not limited to, These include alkyl halides containing electrophiles, sulfonate esters containing electrophiles and olefins containing electrophiles.

Alkyl halides containing electrophiles, sulfonate esters containing electrophiles can be expressed as a general formula L-$R^2$ selected from: L—$CH_2(CHR^3)_m$W, L—$CH_2$(C=O)$R^5$, L—$CHR^4(CR^{4a}R^3)_m$W, L—$CHR^{4a}$(C=O)$R^5$, L—$CHR^{4a}$(P=O)(O$R^6$)$_2$, L—$CHR^{4a}SO_2NH_2$, L—$CHR^{4a}SO_3R^6$,

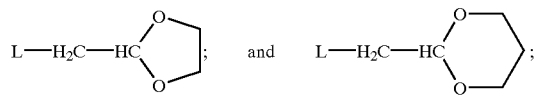

wherein L is a leaving group, $R^3$ is H, F, Cl, Br or $C_1$–$C_6$ alkyl; m is 0–4; W is —$CH_2F$, —$CHF_2$, —$CF_3$, —$CH_2Cl$, —$CHCl_2$, or —$CCl_3$; $R^4$ and $R^{4a}$ are independently H or $C_1$–$C_6$ alkyl, aryl, or aryl-$C_1$–$C_6$ alkyl-; $R^5$ is $C_1$–$C_6$ alkyl, aryl, aryl-$C_1$–$C_6$ alkyl-, —O$R^6$, —$NH_2$, —N($R^6$)$_2$, or —NH$R^6$; $R^6$ is $C_1$–$C_6$ alkyl, aryl, or aryl-$C_1$–$C_6$ alkyl-.

As used herein, the term "leaving group" refers to any group that departs from a molecule in a substitution reaction by breakage of a bond. Examples of leaving groups include, but are not limited to, a halo group (such as chloro, bromo or iodo), a sulfonate ester group (such as methylsulfonyloxy, p-toluylsulfonyloxy or trifluoromethylsulfonyloxy).

An olefin containing an electrophilic center is selected from: $CH_2$=$CH_2$(C=O)$R^5$, $CHR^4$=$CHR^{4a}$(C=O)$R^5$, $CHR^4$=$CHR^{4a}$(P=O)(O$R^6$)$_2$, $CHR^4$=$CHR^{4a}SO_2NH_2$, and $CHR^4$=$CHR^{4a}SO_3R^6$; wherein $R^4$ and $R^{4a}$ are independently H or $C_1$–$C_6$ alkyl, aryl, or aryl-$C_1$–$C_6$ alkyl-; $R^5$ is $C_1$–$C_6$ alkyl, aryl, aryl-$C_1$–$C_6$ alkyl-, —O$R^6$, —$NH_2$, —N($R^6$)$_2$, or —NH$R^6$; $R^6$ is $C_1$–$C_6$ alkyl, aryl, or aryl-$C_1$–$C_6$ alkyl-.

As used herein, the term "base" refers to any agent that reacts with a phenylthio boronate of Formula (I) followed by eletrophilic addition of a hydrocarbon containing an electrophilic center to form a compound of Formula (II) in Scheme 2. Preferred bases for the electrophilic addition are hindered bases. Examples of hindered bases include, but are not limited to, LDA (lithium diisopropylamide), lithium 2,2,6,6-tetramethylpiperidine, lithium hexamethyldisilazane and n-butyllithium. Metal counterions other than lithium such as sodium and potassium can be used.

As used herein, the term "alkylating agent" refers to any agent that alkylates the sulfur of a compound of Formula (II) to form the corresponding sulfonium salt (III). Examples of alkylating agents include, but are not limited to, $C_1$–$C_6$ alkyl halides, trimethyloxonium tetrafluoroborate, dimethylsulfate and methyltriflate. Examples of $C_1$–$C_6$ alkyl halides include, but are not limited to, methyl iodide, ethyl iodide, methyl bromide, and ethyl bromide. Other alkylating agents will be apparent to those of skill in the art, once armed with the present disclosure.

As used herein, the term "metal halide" refers to any halide salt of a alkali metal or an alkaline-earth metal, for example, Na, K, Li, Mg and Ca, that can effect the formation of a compound of Formula (IV). Examples of metal halides include, but are not limited to, sodium iodide, lithium bromide and potassium iodide.

As used herein, the term "hydrogenation agent" refers to any agent or any combination of agents that catalyzes reduction reaction of the corresponding azide of a compound of Formula (IV) to form a compound of Formula (V). Examples of hydrogenation agents include, but are not limited to, a combination of hydrogen with palladium-carbon, stannous chloride in methanol, or alkali metal sulfides such as sodium sulfide and potassium sulfide.

As used herein, the term "strong acid" refers to an acid which essentially reacts completely with water to give a hydronium ion. Examples of strong acids include, but are not limited to, hydrochloric acid, trifluoroacetic acid, sulfonic acid, nitric acid, and sulfuric acid.

"Alkyl" or "alkylene" as used herein is intended to include both branched and straight chain saturated aliphatic hyrdocarbon groups having one to twelve carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl. "Halo" or "halogen" as used herein refers to fluoro, chloro, bromo and iodo. "Counterion" is used to represent a small, negatively charged species such as chloride, bromide, hydroxide, acetate, sulfate, and the like. "Metal counterion" is used to represent metal ion species.

"Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)). Examples of haloalkyl include, but are not limited to, difluoromethyl, trifluoromethyl, dichloromethyl, trichloromethyl, pentafluoroethyl, pentachloroethyl, 2,2-difluoroethyl, 2,2,2-trifluoroethyl, 2,2-dichloroethyl, 2,2,2-trichloroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

As used herein, the term "aryl", or "aromatic residue", is intended to mean an aromatic moiety containing 6, 10 or 14 carbon atoms, preferably 6 or 10 carbon atoms. A particularly preferred aryl moiety is the phenyl group. The aryl group is optionally substituted by 0–5 substituents independently selected from halogen, $C_1$–$C_3$ alkyl, and an electron-withdrawing group.

As used herein, the term "electron wihdrawing group" has its normal meaning as chemical functionality which electronically or inductively causes the withdrawal of electron density from the moiety to which the electron withdrawing groups is attached. Representative electron withdrawing groups include, but are not limited to, nitro groups, halogens, cyano, carboxyl groups and substituted carboxy groups such as ester groups and amido groups. Other electron withdrawing groups will be apparent to those of skill in the art, once armed with the present disclosure.

As used herein, the term "aryl-$C_1$–$C_6$ alkyl-" refers to a $C_1$–$C_6$ alkyl group which bears an aryl group, for example, benzyl group.

As used herein, "cyclic boronic ester" is intended to mean a stable cyclic boronic moiety of general formula —B(OR)(OR) wherein the two R substituents taken together contain from 2 to 20 carbon atoms, and optionally, 1, 2, or 3 heteroatoms which can be N, S, or O. Cyclic boronic esters are well known in the art. Examples of cyclic boronic ester include, but are not limited to, pinanediol boronic ester, pinacol boronic ester, 1,2-ethanediol boronic ester, 1,3-propanediol boronic ester, 1,2-propanediol boronic ester, 2,3-butanediol boronic ester, 1,2-diisopropylethanediol boronic ester, 5,6-decanediol boronic ester, 1,2-dicyclohexylethanediol boronic ester, diethanolamine boronic ester, and 1,2-diphenyl-1,2-ethanediol boronic ester.

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

The methods of the present invention, by way of example and without limitation, may by further understood by reference to Schemes 2–4. Schemes 2–4 detail the general synthetic methods for the preparation of α-aminoboronic acids.

It is to be understood that one skilled in the art of organic synthesis could follow the methods described or exemplified herein to prepare homologs of compounds of Formula (II) through (V), by appropriately choosing a hydrocarbon containing an electrophilic center.

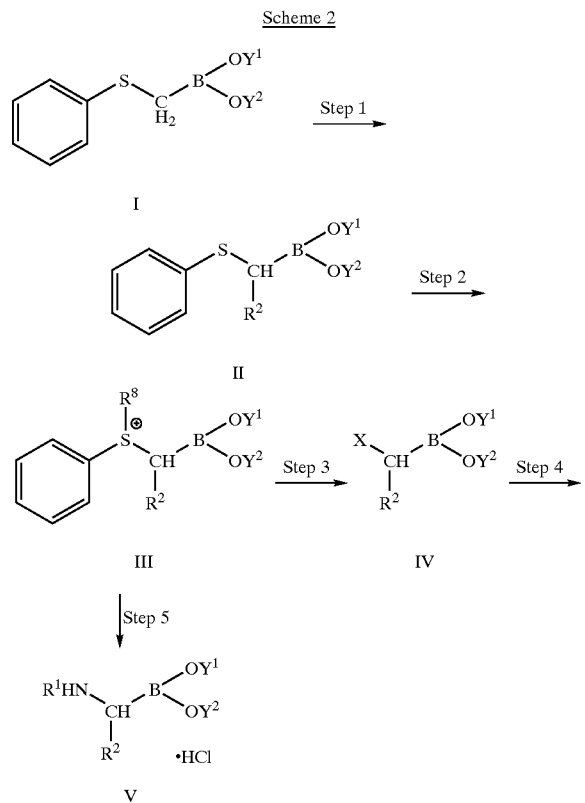

Scheme 2

It is the object of the present invention to provide a novel procedure for the preparation of α-aminoboronic acids, which are useful as intermediates in the synthesis of peptide bronic acids which are highly effective inhibitors of the serine proteases, leukocyte elastase, pancreatic elastase, cathepsin G, and chymotrypsin. More specifically, the α-aminoboronic acids are useful as intermediates for the synthesis of Hepatitis C Virus (HCV) protease inhibitors.

Step 1: Addition: Preparation of Compound of Formula (II)

This step comprises reacting a compound of Formula (I) with a base followed by a hydrocarbon containing an electrophilic center to form a compound of Formula (II). By way of general guidance, one equivalent of compound (I) is treated with one equivalent or about 5–20% excess of a base in a suitable solvent at a reduced temperature (about −20 to about 0° C.) to form the salt of compound (I). Optionally but preferably, salt formation is accompanied by the formation of a precipitant. The mixture is optionally stirred for 15 minutes to 5 hr at about −10 to about 0° C., but not limited to this range. Suitable temperature range can be determined by one skilled in the art by following the methods described herein. Preferably, the mixture is stirred for 30 minutes to 4 hrs at about 0° C. The desired electrophile is dissolved in a suitable inert solvent and added to the salt of compound (I)

dropwise at about −20 to about 10° C., preferably, about −10 to about 0° C. Preferred ratio of the desired electrophile to the salt is 2–5 equivalents of electrophile vs. salt of compound (I). However, much large excess of the electrophile can be used. The mixture is slowly allowed to come to room temperature and to stir overnight.

Preferred bases for Step (1) are hindered bases include LDA (lithium diisopropylamide), lithium 2,2,6,6-tetramethylpiperidine, lithium hexamethyldisilazane and n-butyllithium. More preferred hindered bases are LDA (lithium diisopropylamide), lithium 2,2,6,6-tetramethylpiperidine, lithium hexamethyldisilazane. Metal counterions other than lithium such as sodium and potassium can be used.

Preferred suitable solvents for Step (1) include THF, dimethoxyethane, N,N-dimethylformamide, dimethylsulfoxide, N-methylpyrrolidine, hexamethylphosphoric triamide and hexane. A more perferred suitable solvent is THF. Reagent which binds the metal cation such as HMPA (hexamethyphosphoric triamide), TMEDA (tetramethylethylene diamine), and crown ethers can be added.

The $R^2$ substituent in Scheme 2 is introduced as an electrophile. These include alkyl halides containing electrophiles, sulfonate esters containing electrophiles and olefins containing electrophiles, wherein the olefin is limited to compounds that are good Michael acceptors.

The $R^2$ substituent can be introduced from a hydrocarbon containing an electrophilic center $L-R^2$ selected from: $L-CH_2(CHR^3)_mW$, $L-CH_2(C=O)R^5$, $L-CHR^4(CR^{4a}R^3)_mW$, $L-CHR^{4a}(C=O)R^5$, $L-CHR^{4a}(P=O)(OR^6)_2$, $L-CHR^{4a}SO_2NH_2$, $L-CHR^{4a}SO_3R_6$,

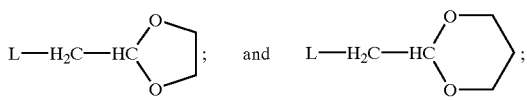

wherein L is a leaving group, $R^3$ is H, F, Cl, Br or $C_1-C_6$ alkyl; m is 0–4; W is $-CH_2F$, $-CHF_2$, $-CF_3$, $-CH_2Cl$, $-CHCl_2$, or $-CCl_3$; $R^4$ and $R^{4a}$ are independently H or $C_1-C_6$ alkyl, aryl, or aryl-$C_1-C_6$ alkyl-; $R^5$ is $C_1-C_6$ alkyl, aryl, aryl-$C_1-C_6$ alkyl-, $-OR^6$, $-NH_2$, $-N(R^6)_2$, or $-NHR^6$; $R^6$ is $C_1-C_6$ alkyl, aryl, or aryl-$C_1-C_6$ alkyl-. Preferred $L-R^2$ for the Step (1) are $L-CH_2(CH_2)_mW$, $L-CH_2(C=O)R^5$. Preferred leaving groups are I, Br, Cl, methylsulfonyloxy, p-toluylsulfonyloxy or trifluoromethylsulfonyloxy. More preferred leaving groups are I or Br. Preferred W is $-CHF_2$ or $-CF_3$. Preferred m is 0, 1 or 2. Preferred $R^5$ is $-OR^6$. More preferred $R^5$ is $-OR-Me$ and $-O-^tBu$.

The $R^2$ substituent can also be introduced from an olefin containing an electrophilic center selected from: $CH_2=CH_2(C=O)R^5$, $CHR^4=CHR^{4a}(C=O)R^5$, $CHR^4=CHR^{4a}(P=O)(OR^6)_2$, $CHR^4=CHR^{4a}SO_2NH_2$, and $CHR^4=CHR^{4a}SO_3R^6$; wherein $R^4$ and $R^{4a}$ are independently H or $C_1-C_6$ alkyl, aryl, or aryl-$C_1-C_6$ alkyl-; $R^5$ is $C_1-C_6$ alkyl, aryl, aryl-$C_1-C_6$ alkyl-, $-OR^6$, $-NH_2$, $-N(R^6)_2$, or $-NHR^6$; $R^6$ is $C_1-C_6$ alkyl, aryl, or aryl-$C_1-C_6$ alkyl-. Preferred olefin containing an electrophilic center is $CH_2=CH_2(C=O)R^5$. Preferred $R^5$ is $-OR^6$. More preferred $R^5$ is $-O-Me$ and $-O-^tBu$. More preferred $R^5$ is $-O-Me$ and $-O-^tBu$.

Optionally compounds containing a carbonyl can be introduced protected with known protecting groups (Greene and Wuts "Protective Groups in Organic Synthesis" 3d edition, John Wiley and Sons, Inc, New York, 1999). 2-Bromomethyl-1,3-dioxolane can be readily applied as $L-R^2$.

It is understood that one skilled in the art can determine the preferred reaction of Step (1) as dependent on temperature, solvent, hindered base, and electrophile.

Step 2: Alkylation: Preparation of Compound of Formula (III)

This step comprises reacting a compound of Formula (II) with an alkylating agent to form a compound of Formula (III). By way of general guidance, one equivalent of compound (II) is treated with one equivalent to excess of an alkylating agent in a suitable solvent to form the corresponding sulfonium salt (III). Preferably, the ratio of compound (II) to alkylating agent is 1:20. The reaction is preferred at reflux, but may be run at room temperature. Suitable temperature range is dependent on the solvent used, can be determined by one skilled in the art by following the methods described herein. Reaction times range from 3 hrs to 5 days, preferably, 3–8 hrs.

Preferred alkylating agents for Step (2) include $C_1-C_6$ alkyl halides, trimethyloxonium tetrafluoroborate, dimethylsulfate and methyltriflate. More preferred alkylating agents are methyl iodide, ethyl iodide or trimethyloxonium tetrafluoroborate.

Preferred suitable solvents for Step (2) include acetonitrile, N,N-dimethylformamide, dimethylsulfoxide, N-methylpyrrdidine, hexamethylphosphoric triamide, THF, and dimethoxyethane. A more preferred suitable solvent is acetonitrile.

Step 3: Halogenation: Preparation of Compound of Formula (IV)

This step comprises reacting a compound of Formula (III) with a metal halide to form a compound of Formula (IV). By way of general guidance, one equivalent of compound (III) is treated with 1 to 10 equivalent of an metal halide in a suitable solvent to form the α-halide (IV) for 1–8 hrs, preferably 6 hrs. The preferred ratio of compound (III) to metal halide is 1:2. The reaction is preferred at reflux, but may be run at room temperature. Suitable temperature range is dependent on the solvent used, can be determined by one skilled in the art by following the methods described herein. Preferred metal halides for Step (3) are sodium iodide, lithium bromide or potassium iodide. A more preferred metal halide is sodium iodide.

Preferred suitable solvents for Step (3) include acetonitrile, N,N-dimethylformamide, dimethylsulfoxide, N-methylpyrrdidine, hexamethylphosphoric triamide, THF, and dimethoxyethane. A more preferred suitable solvent is acetonitrile.

Alternatively, the corresponding sulfonium salt (III) can be generated in situ and the α-halide formed by treatment with an alkyl halide in the presence of a metal halide.

Step 4: Amination: Preparation of Compound of Formula (V).

This step comprises converting a compound of Formula (IV) to a compound of Formula (V). Two different methods are feasible for Step (4). By way of general guidance, the first method comprises reacting one equivalent of compound (IV) with 1 equivalent to excess of lithium hexamethyldisilazane followed by treatment with a strong acid to form the α-aminoboronic acid ester as an amine salt (V). The preferred ratio of compound (IV) to lithium hexamethyldisilazane is 1:1. Compound (IV) is treated with lithium hexamethyldisilazane for 3–8 hrs, at about −100 to −20° C., preferably −78° C. The treatment with an excess at least 3 equivalents of a strong acid is performed at about −100 to 0° C. Preferred strong acids for Step (4) are anhydrous HCl or trifluoroacetic acid.

The second method is particularly feasible for preparing compounds which have acidic protons like the α and β carboxylate esters leading to H-boroAsp(OMe)-pinanediol and H-boroGlu(OMe)-pinanediol. By way of general guidance, compound (IV) is treated with sodium azide followed by reduction with a hydrogenation agent. Preferred methods of reducing the azide are catalytic hydrogenation in the presence of an acid or reduction with stannous chloride in methanol. Preferred catalytic hydrogenation is contacting the azide compound of (IV) with hydrogen and palladium-carbon. The preferred method of synthesis of the azide is to react compound (IV) with a sodium azide in N,N'-dimethylformamide for several hours at 60–80° C. Alternately, the azide can be prepared using phase transfer conditions in which methylene chloride, water, tetrabutylammonium bromide, and sodium azide are used (Matteson et al. *J. Am. Chem. Soc.* 108 810–819, 1986).

Step 5: Direct Amination: Preparation of Compound of Formula (V) Direct from Compound of Formula (III)

As an alternative to formation of the iodide, sulfonium salt (III) can be reacted directly with lithium hexmethyldisilazane or sodium azide to provide intermediates leading to the α-amino compound as discussed in the the above description.

The value of the reaction protocol in Scheme 2 is exemplified by the synthesis of an α-aminoboronic acid with a 2,2-difluoroethyl sidechain shown in Scheme 3.

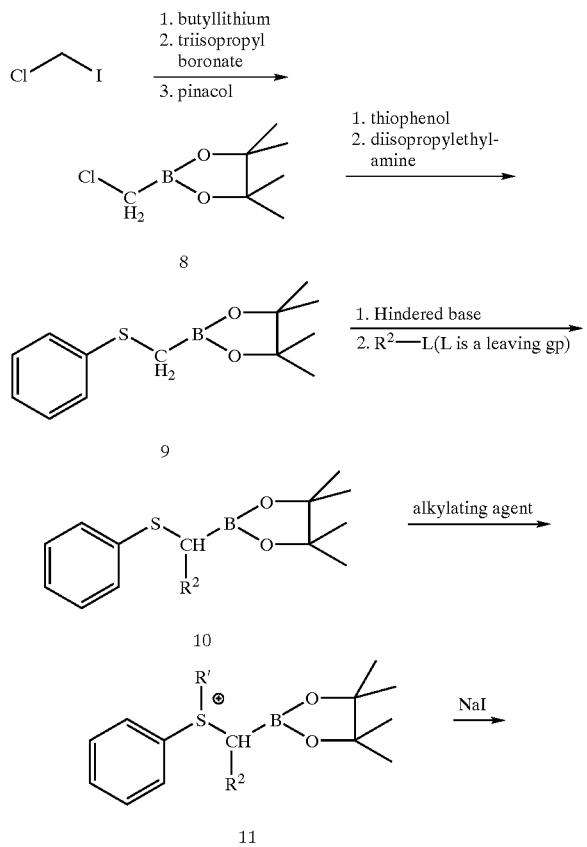

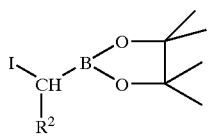

12

Compound 11 or Compound 12

1. $(Me_3Si)_2N^-Li^+$
2. HCl
3. pinanediol

Or
1. $NaN_3$
2. $H_2$, Pd/C
3. pinanediol

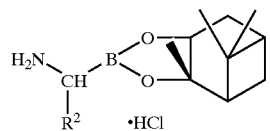

13

1-Chloromethyl boronate pinacol ester 8 is readily prepared by literature procedures, Sadhu and Matteson *Organometallics* 4 1687–1689, 1985. Compound 8 can be readily converted to the corresponding iodide by treatment with sodium iodide. Either alkyl halide readily reacts with thiolphenol in the presence of a tertiary amine to give the corresponding thiol ether 9. Alternately, the thiol ether can be prepared by reacting the lithium salt of thioanisole with a trialkyl boronate as described by Matteson and Arne *Organometallic* 1 280–288, 1982. Transesterification with pinacol gives compound 9.

1-Bromo-2,2-difluoroethane was reacted with the anion of 9 to give 10 where $R^2$ is 2,2-difluoroethyl. The desired product, 1-amino-3,3-difluoropropane boronate 13 was obtained by treating 11 with methyl iodide in the presence of iodide ion followed by lithium hexamethyldisilazane and HCl.

In the present invention, the conversion of 10 to 12 is optimized to obtain the desired α-iodo derivative in quantitative yield. The phenylthio boronic ester 10 is refluxed in acetonitrile under anhydrous conditions for as little as 3 hours and the α-iodo boronic ester is obtained without the formation of elimination products.

The isolation and characterization of the alkylated (sulfonium)boronic ester 11 is a novel reaction. The displacement of the sulfonium ion boronates with nucleophiles is also a novel procedure.

The utility and versatility of the chemistry outlined in Scheme 2 is further demonstrated in the preparation of H-boroAsp(O'Bu)-pinanediol and H-boroGlu(OMe)-pinanediol. For the preparation of the former ($R^2$=—$CH_2$—CO—O'Bu), 9 is allowed to react with t-butyl bromoacetate to give an intermediate with a carboxylmethyl sidechain. Following the steps in Scheme 2, the iodide 12 is obtained. 12 is converted to the amine by treatment with sodium azide followed by catalytic hydrogenation to give 13, H-boroAsp(O'Bu)-$C_{10}H_{16}$·HCl. This compound is readily incorporated into peptides and the sidechain protecting group is removed with anhydrous HCl to give peptide-boroAsp-$C_{10}H_{16}$. Similarly, H-boroAsp(OMe)-$C_{10}H_{16}$ can be synthesized from methyl bromoacetate and the final product is obtained by treating the sidechain methyl ester with potassium trimethylsilanolate (Laganis and Chenard *Tetrahedron Letters*

25, 5831–5834, 1984). H-boroGlu(OMe)-$C_{10}H_{16}$ is also readily prepared by a similar series of reactions (Scheme 4).

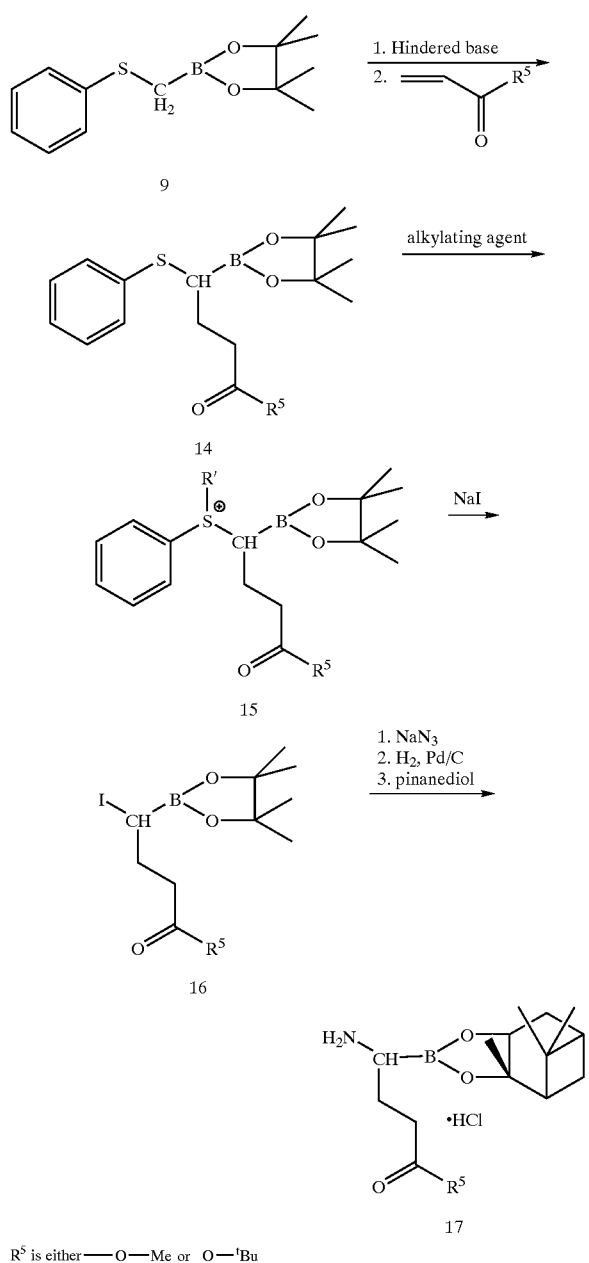

Scheme 4

$R^5$ is either —O—Me or O—$^t$Bu

After treatment of 9 with base to generate the anion at the α-position, a Michael acceptor (in this case methyl acrylate) is added to give 14 where the sidechain is —$CH_2$—$CH_2$—C(O)OMe. Note that the desired product 10 was not obtained when Br—$CH_2$—$CH_2$—COO$^t$Bu was allowed to react with the anion of 9 in Scheme 3. Apparently, this is due to the acidity of the protons alpha to the carboxylate resulting in elimination products. 14 is converted to H-boroGlu(OMe)-$C_{10}H_{16}$ 17 which is readily incorporated into peptides. The sidechain methyl ester is cleaved with potassium trimethylsilanolate. Both boroAsp-$C_{10}H_{16}$ and boroGlu-$C_{10}H_{16}$ peptides can be converted to the corresponding boroAsn-$C_{10}H_{16}$ and -boroGln-$C_{10}H_{16}$ by treating the sidechain carboxylate with ammonia.

In the preparation of H-boroGlu(O$^t$Bu)-$C_{10}H_{16}$, 10 (or 14 in Scheme 4) was not obtained when the anion of 9 was allowed to react with t-butyl 3-bromopropionate due to the formation of elimination products. However, as shown in Scheme 4 the anion of 9 readily adds to Michael acceptors (in this case methyl acrylate). The sequence of reactions shown in Schemes 3 and 4 has made it possible to prepare much more structurally diverse α-aminoboronic acids. In addition to the specific compounds we have prepared, higher order acrylates or alkyl halides can be used to give more complex sidechains. This is particularly valuable for the preparation of compounds with sidechains containing sensitive groups such as ketones, phosphonates and sulfonamides.

The preferred boronic acid protecting group for the syntheses in Schemes 3 and 4 is pinacol. However, after the conversion of either 12 or 16 to the amine, the pinacol ester is readily converted by methods known to one skilled in the art to the pinanediol ester that is more compatible with further synthetic steps.

The —$CH_2$–$CH_2$—COO$^t$Bu substituted boronic ester is treated with anydrous trifluoroacetic acid in dichloromethane (1:1) for 1 hour at room temperature to obtain the sidechain free acid. Both the boroAsp and boroGlu free acids can be obtained in this manner.

The —$CH_2$—$(CH_2)_m$—COOMe substituted α-amino boronic ester is first acylated or coupled to a peptide to protect the free amine. It is then treated with potassium trimethylsilanolate (5 equivalents) in dichloromethane for 6 hours at room temperature to obtain the sidechain free acid. Both the boroAsp and boroGlu free acids can be obtained in this manner.

Compounds of the present invention can effectively be used as inhibitors of protease which do not require an extended peptide sequence such as the aminopeptidases described in Shenvi U.S. Pat. No. 4,537,773, 1985. The new α-aminoboronic acids can be readily incorporated into peptides using methods known to those skilled in the art (Stewart and Young "Solid Phase Peptide Synthesis" Pierce Chemical Co., Rockford Ill., 1984) and used as inhibitors of endopeptidases such as hepatitis C protease. Compounds containing a carboxylate ester sidechain can be further modified by removing the ester protecting groups to yield peptide-boroAsp-pinanediol and peptide-boroGlu-pinanediol for example. Peptide-aminoboronic acid esters containing a free sidechain carboxylate can be coupled with ammonia or primary or secondary amine using standard coupling procedures know in peptide chemistry, Stewart and Young, 1984. Compounds can be tested in biological systems as inhibitors of proteases as free boronic acid or as pinanediol or pinacol esters. All three give comparable results due to the rapid hydrolysis of pinanediol and pinacol esters to the free boronic acid, Kettner and Shenvi J. Biol. Chem. 259, 15106–15114, 1984. However, methods exist which allow the preparation of the free boronic acid, Kettner U.S. Pat. No. 5,384,410 (1995). The boronic acid ester is suspended in 1.0 mM aqueous HCl and is allowed to react with an excess of phenyl boronic acid added in an equal volume of ether. The product is readily separated from phenyl boronic acid and phenyl boronic acid pinanediol ester by extracting with ether. The free boronic acid is obtained by lyophilizing the aqueous phase. Pinanediol esters are also readily removed by treating with anhydrous boron trichloride in methylene chloride as described by Kinder et al., J. Med. Chem. 28, 1917–1925 (1985). The boronic acid ester is treated with a 2–3 fold excess of $BCl_3$ for 5 min at −78° C. and the mixture is allowed to stir 15 min in a 0° ice bath. Excess BCl₃ is hydrolyzed by the slow addition of water. Less structurally rigid boronic acid esters such as pinacol esters can be prepared by transesterification with diethanolamine and by hydrolyzing the diethanolamine ester with aqueous acid (Kettner and Shenvi *J. Biol. Chem.* 259, 15106–15114, 1984). Free boronic acid can be converted to the difluoroborane (—BF₂) using a modification of the procedure of Kinder et al., *J. Med. Chem.* 28, 1917–1925 (1985). The boronic acid is treated with a 5-fold molar excess of 0.50 N aqueous hydrofluoric acid at room temperature. Excess hydrofluoric acid and water are removed by lyophilization to give the desire product.

The following examples are meant to be illustrative of the present invention. These examples are presented to exemplify the invention and are not to be construed as limiting the invention's scope.

EXAMPLE 1

Synthesis of 1-Phenylthio-1-(2,2-difluoroethyl) methyl-1-boronatepinacol Ester (See 10, Scheme 3)

(Step 1a) Chloromethyl Boronate Pinacol Ester

THF(150 mL) was placed in a 1 L, 3 neck flask equipped with two addition funnels. Triisopropyl borate (Aldrich) (32.1 mL, 139 mmol) and chloro-iodomethane (Aldrich) (10.3 mL, 142 mmol) were added to the flask. The reaction mixture was cooled to −78° C. n-Butyllithium (81.9 mL, 131 mmol, 1.6 M in hexanes) was added dropwise to the flask via an addition funnel. The solution was stirred at −78° C. for 2 hours and then gradually warmed to −10° C. A crystal of methyl orange was added to the reaction. Hydrogen chloride (1.0 N in ether) was added via the other addition funnel until the methyl orange end point was reached. Pinacol (16.4 g, 139 mmol) was added to the flask and the reaction mixture was stirred for 12 hours. It was then concentrated in vacuo and distilled (bp 61–63° C., 5 mm Hg) to give 16.0 g (65%) of the desired compound as a yellow oil. $^1$H NMR (CDCl₃) δ 2.97 (s, 2H, ClCH₂B), 1.29 (s, 12H, CCH₃).

(Step 1b) Iodomethyl Boronate Pinacol Ester

THF (800 mL) was placed in a 3 L, 3-necked flask equipped with two addition funnels. Triisopropyl borate (Aldrich) (128 mL, 0.55 mol) and chloro-iodomethane (Aldrich) (100 g, 0.56 mol) were added. The mixture was cooled to −78° C. and n-butyl lithium (330 mL, 0.53 mol, 1.6 M in hexanes) was added dropwise. The solution was stirred for 2 hrs and slowly allowed to warm to −10° C. Methyl orange indicator was added and HCl (1.0 M in ether) was added until the methyl orange endpoint was reached. Pinacol (65 g, 0.55 mol) was added and reaction mixture was allowed to stir 12 hrs. It was filtered and evaporated in vacuo. The residue was dissolved in acetone (500 mL) and sodium iodide (70 g, 0.47 mol) was added. After stirring for 12 hrs at room temperature, solvent was removed by evaporation and the residue was dissolved in ethyl acetate and washed with saturated aqueous NaCl. The organic phase was dried over Na₂SO₄, filtered, and concentrated in vacuo. It was distilled to give 69 g (47%) of the desired product (bp 45–50° C., 1.5 mm). $^1$H NMR (CDCl₃) δ 2.16 (s, 2H), 1.26 (s, 12H).

(Step 1c) Phenylthiomethane Boronate Pinacol Ester

Thiophenol (11.6 mL, 113 mmol) was dissolved in DMF (40 mL) and diisopropylethylamine (19.8 mL, 113 mmol) and chloromethyl boronate pinacol ester (20 g, 113 mmol) were added sequentially. (Iodomethyl boronate pinacol can be readily substituted for the chloro compound.) After stirring for 12 hours, solvent was removed by rotary evaporation and ether (70 mL) was added. The reaction mixture was washed with 0.2 N HCl (70 mL), 5% NaHCO₃ (70 mL) and saturated sodium chloride (70 mL). The combined organic phases were dried over sodium sulfate and filtered. The filtrate was concentrated in vacuo and distilled (bp 125–127° C., 0.6 mm Hg) to give 21.6 g (76%) of the desired product as a clear oil. $^1$H NMR (CDCl₃) δ 7.32–7.11 (m, 5H), 2.42 (s, 2H), 1.24 (s, 12H)

(Step 1d) 1-Phenylthio-1-(2,2-difluoroethyl)methyl-1-boronatepinacol Ester

Butyllithium (50.6 mL, 126 mmol, 2.5 M in hexanes) was added dropwise to a solution of diisopropylamine (18.4 mL, 133 mmol) dissolved in THF (40 mL) at 0° C. in a 500 mL round bottom flask. A solution of phenylthiomethane boronate pinacol ester (31.6 g, 126 mmol) in THF (40 mL) was added dropwise over a period of approximately 2 min to yield a white precipitate. After stirring for 1 hr at 0° C., 1,1-difluoro-2-bromoethane (Lancaster) (51 mL, 630 mmol) was added dropwise. The precipitate dissolved and the solution was allowed to warm to room temperature and stirred for 16 hrs. Excess cold 10% phosphoric acid was added and the mixture was stirred for 5 min. Ether (100 mL) was added and the phases were separated. The organic layer was dried over sodium sulfate and filtered. The filtrate was concentrated in vacuo and distilled (bp 119–122° C., 0.4 mm Hg) to give 22 g (56%) of product as a clear oil. $^1$H NMR (CDCl₃) δ 7.43–7.19 (m, 5H, C₆H₅), 6.16–5.78 (tt, 1H, CHF₂), 2.82 (m, 1H, SCHB), 2.38–2.19 (m, 2H, CH₂CHF₂), 1.23 (s, 12H, CCH₃). $^{19}$F NMR δ −116.8 to −117.0 (dt, CHF₂).

EXAMPLE 2

1-Phenylthio-1-(3,3,3-trifluoropropyl)methyl-1-boronate Pinacol Ester

The lithium salt of pheylthiomethane boronate pinacol ester (8.0 g, 32 mmol) was prepared by the procedure from Step 1c. 3,3,3-trifluoropropyl iodide (Lancaster) (15.0 g, 64.0 mmol) was added dropwise to the lithium salt at 0° C. After a complete solution was obtained, the reaction mixture was allowed to come to room temperature. The solution was allowed to stir 12 hrs. The product was isolated by the procedure in Example 1a. Final purification by distillation gave the desired product as a clear oil (bp 112–114° C., 0.25 mm Hg) in a yield of 6.53 g (59%). 1H NMR (CDCl₃) δ 7.41–7.11 (m, 5H, C₆H₅), 2.78 (t, 1H, SCHB), 2.35 (m, 2H, CH₂CF₃), 1.98 (m, 2H, CH₂CH₂CF₃), 1.23 (s, 12H, CCH₃). $^{19}$F NMR δ −116.8 to −117.0 (t, CF₃).

EXAMPLE 3

1-Phenylthio-2-t-butoxycarbonylethane-1-boronate Pinacol Ester

Phenylthiomethane boronate pinacol ester was prepared by the procedure from Step 1c. Diisopropylamine (5.8 mL, 42.0 mmol) was dissolved in THF (20 mL) and stirred at 0° C. in a 500 mL round bottom flask. n-Butyllithium (16.0 mL, 40.0 mmol, 2.5M in hexanes) was added dropwise to the solution. A solution of phenylthiomethane boronate pinacol ester (10.0 g, 40.0 mmol) in THF (20 mL) was added dropwise rapidly, yielding a white precipitate. The reaction mixture was stirred for 1 hr at 0° C., followed by the dropwise addition of tert-butyl bromoacetate (Aldrich) (17.7 mL, 120 mmol). The precipitate dissolved and the solution was allowed to warm to room temperature and stirred for 16 hrs. The mixture was then treated with excess cold 10% phosphoric acid and stirred for 5 minutes. The reaction mixture was poured into a separatory funnel and extracted with ether (100 mL). The organic layer was dried over sodium sulfate and filtered. The filtrate was concentrated in vacuo and purified by silica gel eluting with 10% ethyl acetate: hexanes as a solvent to yield a clear colorless oil (4.77 g, 0.014 mol, 34.9%). $^1$H NMR (CDCl$_3$) δ 7.43–7.19 (m, 5H), 2.98 (t, 1H), 2.62 (d, 2H), 1.41 (s, 9H), 1.25 (d, 12H).

EXAMPLE 4

1-Phenylthio-ethylboronate Pinacol Ester (Using 2, 2,6,6-tetramethylpiperidine as a Base)

n-Butyllithium (1.25 mL, 2.0 mmol, 1.6 M in hexanes) was added dropwise to a solution of 2,2,6,6-tetramethylpiperidine (0.33 mL, 2.0 mmol) dissolved in anhydrous hexanes (0.5 mL) at 0° C. in a 10 mL round bottom flask. The reaction mixture was stirred for 10 min. A solution of phenylthiomethane boronate pinacol ester (0.5 g, 2.0 mmol) in hexanes was added dropwise over a period of 5 min to yield a light orange precipitate. After stirring for 1 hr at 0° C., methyl iodide (0.12 mL, 4.0 mmol) was added dropwise. The precipitate dissolved and the solution was allowed to warm to room temperature and stirred for 12 hrs. Excess cold 10% phosphoric acid was added and the mixture was stirred for 5 min. Ether (10 mL) was added and the phases were separated. The organic layer was dried over sodium sulfate and filtered. The filtrate was concentrated in vacuo. Spectral characterization indicated that the desired product was obtained in a yield of 60%. The presence of the desired product and its yield were determined by the presence of NMR signals characteristic of 1-phenylthio-ethylboronate pinacol reported in the literature (Matteson and Arme *Organometallics*, 1, 280–288, 1982). Reported spectrum: $^1$H NMR (CDCl$_3$) δ 7.50 (m, C$_6$H$_5$), 2.99 (q, SCHB), 1.36 (d, CH$_3$), 1.20 (s, CH$_3$ of pinacol). Found: $^1$H NMR (CDCl$_3$) δ 7.37–7.13 (m, 5H, C$_6$H$_5$), 2.99 (q, 1H, SCHB), 1.27 (d, 3H, CH$_3$), 1.23 (s, 12H, CCH$_3$). APCI m/z calculated for C$_{14}$H$_{29}$BO$_2$S+H: 265.2. Found: 265.1.

EXAMPLE 5

1-Phenylthio-ethylboronate Pinacol Ester (Using n-butyllithium as a Base)

n-Butyllithium (1.25 mL, 2.0 mmol, 1.6 M in hexanes) was dissolved in anhydrous THF (0.5 mL) at 0° C. in a 10 mL round bottom flask. The reaction mixture was stirred for 10 min. A solution of phenylthiomethane boronate pinacol ester (0.50 g, 2.0 mmol) in THF was added dropwise over a period of 5 min to yield a light colored precipitate. After stirring for 1 hr at 0° C., methyl iodide (0.12 mL, 4.0 mmol) was added dropwise. The precipitate dissolved and the solution was allowed to warm to room temperature and stirred for 12 hours. Excess cold 10% phosphoric acid was added and the mixture was stirred for 5 min. Ether (10 mL) was added and the phases were separated. The organic layer was dried over sodium sulfate and filtered. The filtrate was concentrated in vacuo and the product characterized by the method described for Example 4. Product was obtained in a yield of 20%. $^1$H NMR (CDCl$_3$) δ 7.37–7.13 (m, 5H, C$_6$H$_5$), 2.99 (q, 1H, SCHB), 1.27 (d, 3H, CH$_3$), 1.23 (s, 12H, CCH$_3$). APCI m/z calculated for C$_{14}$H$_{29}$BO$_2$S+H: 265.2. Found: 265.1.

EXAMPLE 6

1-Phenylthio-ethylboronate Pinacol Ester (Using Lithium Hexamethyldisilazane as a Base)

Lithium hexamethyldisilazane (2.0 mL, 2.0 mmol, 1.0 M in THF) was dissolved in anhydrous toluene (0.5 mL) and cooled to 0° C. in a 10 mL round bottom flask. A solution of phenylthiomethyl boronate pinacol ester (0.50 g, 2.0 mmol) in toluene was added dropwise over a period of 5 min to yield a light yellow precipitate. After stirring for 1 hr at 0° C., methyl iodide (0.12 mL, 4.0 mmol) was added dropwise. The precipitate dissolved and the solution was allowed to warm to room temperature and stirred for 12 hrs. Excess cold 10% phosphoric acid was added and the mixture was stirred for 5 min. Ether (10 mL) was added and the phases were separated. The organic layer was dried over sodium sulfate and filtered. The filtrate was concentrated in vacuo and analyzed by the method described for Example 4. Product was present in a yield of 50%. $^1$H NMR (CDCl$_3$) δ 7.37–7.13 (m, 5H, C$_6$H$_5$), 2.99 (q, 1H, SCHB), 1.27 (d, 3H, CH$_3$), 1.23 (s, 12H, CCH$_3$). APCI m/z calculated for C$_{14}$H$_{29}$BO$_2$S+H: 265.2. Found: 265.1.

EXAMPLE 7

1-Phenylthio-3-methoxycarbonylpropane-1-boronate Pinacol Ester, (Michael Addition to Olefins)

n-Butyllithium (8.0 mL, 20 mmol, 2.5 M in hexanes) was added dropwise to a solution of dmsopropylamine (2.9 mL, 21 mmol) in THF (10 mL) and stirred at 0° C. in a 50 mL round bottom flask. A solution of phenymthiomethane boronate pinacol ester (5.0 g, 20 mmol) in THF (10 mL) was added dropwise yielding a white precipitate. The reaction mixture was stirred for 1 hr at 0° C., followed by the dropwise addition of methyl acrylate (Aldrich) (1.8 mL, 20 mmol). The precipitate dissolved and the solution was allowed to warm to room temperature and stirred for 16 hrs. The mixture was then treated with excess cold 10% phosphoric acid and stirred for 5 min. The product wa s extracted into ether (100 mL). The organic layer was dried over sodium sulfate and filtered. Solvent was evaporated and the residue purified by silica gel chromatography using 10% ethyl acetate: hexanes as a solvent to yield a clear colorless oil (0.67 g, 1.99 mmol, 10.0%). $^1$H NMR (CDCl$_3$) δ 7.43–7.19 (m, 5H), 3.62 (s, 3H), 2.80 (t, 1H), 2.58 (m, 2H), 1.98 (m, 2H), 1.20 (s, 12H).

EXAMPLE 8

1-Iodo-3,3-difluoropropane-1-boronate Pinacol Ester

1-Phenylthio-3,3-difluoropropane-1-boronate pinacol ester (Example 1, 6.0 g, 19 mmol) was dissolved in anhydrous acetonitrile (60 mL) and dry methyl iodide (24 mL, 380 mmol) and sodium iodide (5.8 g, 38 mmol) were added. The reaction mixture was vigorously refluxed for 5 hrs. The solvent was evaporated in vacuo. The residue was partitioned between water (40 mL) and ether (40 mL). The phases were separated and the organic phase was washed with an equal volume of water. The combined organic phases were dried over Na$_2$SO$_4$ and evaporated to give a brown oil which was purified by distillation to give 3.1 g of the desired product (49%), bp 63–65° C., 0.4 mm. $^1$H NMR (CDCl$_3$) δ 6.18–5.79 (tt, 1H, CHF$_2$), 3.21 (t, 1H, ICHB), 2.43–2.21 (m, 2H, CH$_2$CHF$_2$), 1.27 (s, 12H, CCH$_3$).

EXAMPLE 9

1-Iodo-4,4,4-trifluorobutane-1-boronate Pinacol Ester

1-Phenylthio-4,4,4-trifluorobutane-1-boronate pinacol ester (Example 2, 3.3 g, 9.5 mmol) was dissolved in anhydrous acetonitrile (33 mL). Dry methyl iodide (12 mL, 190 mmol) was added, followed by the addition of sodium iodide (2.9 g, 19 mmol). The reaction mixture was refluxed for 12 hrs. Solvent was evaporated and final purification was achieved by distillation. The product was obtained in a yield of 3.3 g (95%, bp 51° C., 0.5 mm Hg). $^1$H NMR (CDCl$_3$) δ 3.21 (t, 1H, ICHB), 2.39 (m, 2H, CH$_2$CF$_3$), 2.05 (m, 2H, CH$_2$CH$_2$CF$_3$), 1.27 (s, 12H), CH$_3$).

EXAMPLE 10

1-iodo-2-t-butoxycarbonylethyl-1-boronate Pinacol Ester

1-Phenylthio-2-t-butoxycarbonylethane-1-boronate pinacol ester (Example 3, 0.76 g, 2.1 mmol) was dissolved in anhydrous acetonitrile (10 mL). Dry methyl iodide (2.6 mL, 42 mmol) was added, followed by the addition of sodium iodide (0.15 g, 4.2 mmol). The reaction mixture was refluxed for 8 hrs. The solvent was evaporated in vacuo. Water (20 mL) was added and the crude product was extracted into ether (20 mL). It was dried over MgSO$_4$ and concentrated using a rotary evaporator. The crude mixture was purified by silica gel chromatography using 40% ethyl acetate: hexanes to yield a brown oil (0.25 g, 0.66 mmol, 31%). $^1$H NMR (CDCl$_3$) δ 3.38 (t, 1H), 2.8 (m, 2H), 1.41 (s, 9H, CCH$_3$), 1.24 (d, 12H).

EXAMPLE 11

Preparation of 1-Iodo-3-methoxycarbonyl-propane-1-boronate Pinacol Ester

1-Phenylthio-3-methoxycarbonylpropane-1-boronate pinacol ester (Example 7, 0.45 g, 1.3 mmol) was dissolved in anhydrous acetonitrile (10 mL). Dry methyl iodide (1.7 mL, 27 mmol) was added, followed by the addition of sodium iodide (0.40 g, 2.7 mmol). The reaction mixture was refluxed for 8 hrs. After evaporating solvent, the reaction mixture was dissolved in ether (20 mL) and was washed with water (20 mL). After drying over MgSO$_4$ and evaporating solvent, the crude product was purified by silica gel chromatography using 20% ethyl acetate: hexanes to yield a brown oil (0.10 g, 0.28 mmol, 21%). $^1$H NMR (CDCl$_3$) δ 3.63 (s, 3H), 3.30 (t, 1H), 2.40 (m, 2H), 2.15 (m, 2H), 1.24 (s, 12H).

EXAMPLE 12

Preparation of 1-iodo-3,3-difluoropropyl Boronate Pinacol Ester (Using Ethyl Iodide as an Alkylating Agent)

1-phenylthio-3,3-difluoropropane-1-boronate pinacol ester (0.10 g, 0.32 mmol) was dissolved in acetonitrile (5 mL). Ethyl iodide (1.0 mL, 13 mmol) and sodium iodide (0.19 g, 1.3 mmol) were added. The reaction was vigorously refluxed for 8 hrs. The solvent was evaporated in vacuo and the residue was partitioned between water (10 mL) and ether (10 mL). The phases were separated and the organic phase was washed with an equal volume of ether. The combined organic phases were dried over Na$_2$SO$_4$ and evaporated to give a light brown oil. Spectral characterization indicated that the desired product was obtained in a yield of 35%. The presence of the desired product and its yield were determined by the presence of NMR signals characteristic of 1-iodo-3,3-difluoropropyl boronate pinacol ester reported in Example 8. $^1$H NMR (CDCl$_3$) δ 6.18–5.79 (tt, 1H, CHF$_2$), 3.21 (t, 1H, ICHB), 2.42–2.21 (m, 2H, CH$_2$CHF$_2$), 1.27 (s, 12H, CCH$_3$).

EXAMPLE 13

Preparation of 1-iodo-3,3-difluoropropyl Boronate Pinacol Ester (Using Trimethyloxonium Tetrafluoroborate as an Alkylating Agent)

1-phenylthio-3,3-difluoropropane-1-boronate pinacol ester (0.10 g, 0.30 mmol) was dissolved in dichloromethane (3 mL). Trimethyloxonium tetrafluoroborate (0.090 g, 0.60 mmol) was added. The reaction was stirred at room temperature for 3 hrs. Saturated sodium chloride was poured into the reaction mixture. The organic phase was isolated and the aqueous phase was washed with dichloromethane. The organic phases were combined and dried over sodium sulfate. Solvent was evaporated in vacuo to give the sulfonium salt as a light brown oil in a yield of 80%. $^1$H NMR (CDCl$_3$) δ 7.78–7.75 (m, 5H), 6.41–6.0 (tt, 1H, CHF$_2$), 3.15 (s, 3H), 2.82 (m, 1H, CHB), 2.20–2.0 (m, 2H, CH$_2$CHF$_2$), 1.27 (s, 12H, CCH$_3$).

The sulfonium ion (0.050 g, 0.15 mmol) was dissolved in acetonitrile (5 mL). Sodium iodide (0.045 g, 0.30 mmol) was added and the reaction mixture was refluxed for 3 hrs. The solvent was evaporated in vacuo. The residue was partitioned between water (10 mL) and ether (10 mL). The phases were separated and the organic phase was washed with an equal volume of water. The combined organic phases were dried over Na$_2$SO$_4$ and evaporated to give a light brown oil. Spectral analysis indicated that the desired product was present in a yield of 30% as determined by the method in Example 8. $^1$H NMR (CDCl$_3$) δ 6.18–5.79 (tt, 1H, CHF$_2$), 3.21 (t, 1H, ICHB), 2.42–2.21 (m, 2H, CH$_2$CHF$_2$), 1.28 (s, 12H, CCH$_3$).

EXAMPLE 14

Preparation of 1-iodo-3,3-difluoropropyl Boronate Pinacol Ester (Using Methyl Iodide as an Alkylating Agent and DMF as a Solvent)

1-phenylthio-3,3-difluoropropane-1-boronate pinacol ester (0.76 g, 2.4 mmol) was dissolved in dimethylformamide (6 mL). Methyl iodide (1.7 mL, 27 mmol) and sodium iodide (0.47 g, 3.2 mmol) were added. The reaction was stirred at a room temperature for 6 days. The solvent was evaporated in vacuo. The residue was partitioned between water (10 mL) and ether (10 mL). The phases were separated and the organic phase was washed with an equal volume of water. The combined organic phases were dried over Na$_2$SO$_4$ and evaporated to give a light brown oil. The desired product was present in a yield of 10% as determined the method in Example 8. $^1$H NMR (CDCl$_3$) δ 6.18–5.79 (tt, 1H, CHF$_2$), 3.21 (t, 1H, ICHB), 2.42–2.21 (m, 2H, CH$_2$CHF$_2$), 1.28 (s, 12H, CCH$_3$).

EXAMPLE 15

Preparation of 1-amino-3,3-difluoropropyl Boronate Pinacol Ester.HCl

1-Iodo-3,3-difluoropropanyl boronate pinacol (Example 8, 2.7 g, 8.1 mmol) was dissolved in THF (10 mL) and was added dropwise to a solution of lithium bis(trimethylsilyl) amide (9.7 mL, 9.7 mmol, 1.0 M in THF) dissolved in anhydrous THF (10 mL) and cooled to −78° C. The reaction mixture was allowed to warm to room temperature and stirred for 12 hrs. It was concentrated in vacuo and hexane was added. The reaction mixture was cooled to −780° C. and 4 N anhydrous hydrogen chloride in dioxane (6.0 mL, 24 mmol) was added dropwise. The mixture was allowed to warm to room temperature and stirred for 5 hrs. The reaction mixture was evaporated and chloroform was added. Insoluble material was removed by filtration. The filtrate was evaporated almost to dryness and hexanes were added. Upon standing the product crystallized. It was isolated and washed with cold hexane to yield 1.1 g (52%), mp 138–141° C. 1H NMR (CDCl$_3$) δ 7.68 (bs, 3H), 6.22–6.01 (tt, 1H), 3.42 (m, 1H), 2.76–2.51 (m, 2H), 1.32 (s, 12H). $^{19}$F NMR δ −115.2 to −115.5 (dt, CHF$_2$). HRMS calculated for C$_9$H$_{18}$B$_1$F$_2$NO$_2$+H: 222.1. Found: 222.1.

EXAMPLE 16

Preparation of 1-amino-4,4,4-trifluorobutyl Boronate Pinanediol Ester

1-Iodo-4,4,4-triflurobutyl boronate pinacol ester (Example 9, 3.4 g, 9.6 mmol) was reacted with lithium bis(trimethylsilyl)amide and HCl by the procedure described in Example 15. The crude product was dissolved in chloroform and insoluble material was removed by filtration. Solvent was removed by evaporation and the residue was dissolved in hexane. On standing the desired product crystallized. $^1$H NMR (CDCl$_3$) δ 7.80 (bs, 3H), 3.19 (m, 1H), 2.78 (m, 1H), 2.58–2.05 (m, 3H), 1.23 (s, 12H) $^{19}$F NMR (CDCl$_3$) δ 66.67 to −66.59 (t, CF$_3$). Analysis calculated for C$_{10}$H$_{19}$BF$_3$NO$_2$+Cl: 288.1. Found: 288.1.

EXAMPLE 17

Preparation of 1-amino-2-t-butoxycarbonylethane-1-boronate Pinanediol Ester.HCl (H-boroAsp(O'Bu)-pinanediol.HCl)

1-Azido-2-t-butoxycarbonylethane-1-boronate pinacol ester was prepared from the iodide in Example 10. To a solution of tetrabutylammonium bromide (0.053 g, 0.16 mmol), dissolved in dichloromethane (60 mL), was added a solution of sodium azide (2.1 g, 32 mmol) dissolved in water (16 mL). The reaction mixture was vigorously stirred as 1-iodo-2-t-butoxycarbonylethyl-1-boronate pinacol ester (Example 10, 1.2 g, 3.2 mmol), dissolved in dichloromethane (13 mL), was added dropwise. The reaction was stirred for 10 hrs. After removing solvent by evaporation, saturated ammonium chloride was added and the product was extracted into methylene chloride (30 mL). It was dried over MgSO$_4$ and concentrated using a rotary evaporator to give a yellow oil. $^1$H NMR (CDCl$_3$) δ 3.35 (t, 1H), 2.60 (d, 1H), 1.43 (s, 9H), 1.27 (s, 12H).

The pinanediol ester was prepared by transesterifcation. The pinacol ester (0.90 g, 3.0 mmol) was dissolved in THF (5 mL) and pinanediol (0.56 g, 3.3 mmol) was added. After stirring for 2 hours, solvent was evaporated and the residue purified by silica gel chromatography using 95% hexanes: ethyl acetate. The product was obtained as a light brown oil (0.62 g, 1.8 mmol, 58%). TLC in hexanes: ethyl acetate (17:3) indicated a single spot, R$_F$ 0.43. $^1$H NMR (CDCl$_3$) δ 4.2 (tt, 1H), 3.41 (m, 1H), 2.61 (m, 2H), 2.40–1.85 (m, 6H), 1.43 (s, 9H), 1.40(s, 3H), 1.31 (s, 3H), 0.81 (s, 3H).

The amine was obtained by catalytic hydrogenation of the azide. 1-azido-2-t-butoxycarbonylethane-1-boronate pinanediol ester (50 mg, 0.29 mmol) was dissolved in methanol (100 mL) and hydrogen chloride (4 N solution in dioxane) (0.040 mL, 0.32 mmol) and 10% palladium on carbon were added. The azide was hydrogenated at 55 psi for 2 hrs. The catalyst was removed by filtration and solvent was evaporated. Cold hexanes were added to give a solid. It was dried under high vacuum to give the final product (0.080 g, 0.23 mmol, 79%). $^1$H NMR (CDCl$_3$) δ 4.25 (t, 1H), 3.05 (t, 1H), 2.78 (m, 2H), 2.4–1.85 (m, 6H), 1.42–1.25 (2s, 12H), 0.82 (s, 3H). Analysis calculated for C$_{17}$H$_{30}$BNO$_4$+H: 324.3. Found: 324.3.

EXAMPLE 18

Preparation of 1-amino-3-methoxycarbonyl-propane-1-boronate Pinanediol Ester

The azide was prepared by displacing the iodide under anhydrous conditions in DMF. To a solution of 1-iodo-3-methoxycarbonylpropane-1-boronate pinacol ester (Example 11, 0.10 g, 0.28 mmol) dissolved in N,N-dimethylformamide (1 mL) was added sodium azide (0.037 g, 0.56 mmol) The reaction mixture was heated at 68° C. for 3 hrs. The solvent was evaporated in vacuo. The residue was dissolved in ethyl acetate and was washed with water (2×3 mL). It was dried over MgSO$_4$ and evaporated to give a brown oil. $^1$H NMR (CDCl$_3$) δ 3.63 (s, 3H), 3.20 (t, 1H), 2.58 (m, 1H), 1.98 (m, 2H), 1.27 (s, 12H).

1-Azido-3-methoxycarbonylpropane-1-boronate pinanediol ester was prepared from the pinacol ester. The pinacol ester (0.42 g, 1.56 mmol) was dissolved in ether (5 mL) and pinanediol (0.29 g, 1.72 mmol) was added. The reaction was stirred for 2 hrs. Purified by silica gel chromatography using 80% hexanes: ethyl acetate gave the desired product as a light brown oil (0.13 g, 0.41 mmol, 26%). TLC using hexanes: ethyl acetate (8:2) indicated a single spot, R$_F$ of 0.37. $^1$H NMR (CDCl$_3$) δ 4.20 (dd, 1H), 3.61 (s, 1H), 3.21(m, 1H), 2.51–1.82 (m, 1OH), 1.43 (s, 3H), 1.32(s, 3H), 0.81 (s, 3H).

1-Amino-3-methoxycarbonylpropane-1-boronate pinanediol was prepared by reduction of the corresponding azide. The azide (0.078 g, 0.24 mmol) was dissolved in methanol (4 mL) and hydrogen chloride (4 N in dioxane 0.0060 mL, 0.24 mmol) was added and 10% palladium on carbon were added and mixture was hydrogenated at atmospheric pressure for 2 hours. After removing the catalyst and evaporation of solvent, the residue was dried under high vacuum to give the desired product (0.040 g, 0.13 mmol, 55%). $^1$H NMR (CDCl$_3$) δ 4.25 (d, 1H), 3.11 (m, 1H), 2.61–1.85 (m, 10H), 1.42 (s, 3H), 1.32 (s, 3H), 0.82 (s, 3H). Analysis calculated for C$_{15}$H$_{26}$BNO$_4$+H: 296.4. Found: 296.4.

EXAMPLE 19

Preparation of 1-(benzophenone imino)-,3,3-difluoropropyl Boronate Pinacol as an Intermediate for the Preparation of 1-Amino-3,3-difluoropropyl Boronate Pinacol n-Butyllithium (0.080 mL, 0.13 mmol, 1.6 M in hexanes) was added dropwise to a solution of benzephenone imine (0.020 mL, 0.14 mmol) dissolved in anhydrous THF (2 mL) at 0° C. The orange reaction mixture was stirred for 0.5 h. A solution of 1-iodo-3,3-difluoropropyl boronate pinacol (Example 12, 0.040 g, 0.13 mmol) was added dropwise over a period of 5 minutes. The reaction mixture was allowed to warm to room temperature and stirred for 8 hours. The solvent was evaporated in vacuo. The residue was redissolved in ethyl acetate and washed with 0.2 N HCl. The organic phase was dried (Na$_2$SO$_4$), filtered and concentrated to give the desired imine. $^1$H NMR (CDCl$_3$) δ7.99–7.40 (m, 10H, C$_{12}$H$_{10}$C=N), 6.23–5.79 (tt, 1H, CHF$_2$), 3.80 (t, 1H, CHB), 2.38–2.10 (m, 2H, CH$_2$CHF$_2$), 1.28 (s, 12H, CCH$_3$). Analysis calculated for C$_{22}$H$_{26}$O$_2$NBF$_2$+H: 386.2. Found: 386.4.

Table 1 provides representative Examples of the compounds of Formula (V) of the present invention.

TABLE 1

$$H_2N-\underset{\underset{B}{|}}{\overset{R^2}{C}}\begin{array}{c}OY^1\\OY^2\end{array}$$

| Ex. | R² | B(OY¹)(OY²) | MS (M + H)⁺ |
|---|---|---|---|
| 15 | 3,3-difluoroethyl | pinacol boronic ester | 222.1 |
| 16 | 4,4,4-trifluoropropyl | pinanediol boronic ester | 253.1 |
| 17 | t-butoxycarbonylmethyl | pinanediol boronic ester | 324.3 |
| 18 | 2-methoxycarbonyl-ethyl | pinanediol boronic ester | 296.4 |

Although the present invention has been described with respect to specific embodiments, the details of these embodiments are not to be construed as limitations. Various equivalents, changes and modification may be made without departing from the spirit and the scope of this invention, and it is understood that such equivalent embodiments are part of this invention. The present invention may be embodied in other specific forms without departing from the spirit or essential attributes thereof and, accordingly, reference should be made to the appended claims as further indicating the scope of the invention.

What is claimed is:

1. A process for the synthesis of a compound of Formula (V):

$$H_2N-\underset{\underset{B}{|}}{\overset{R^2}{CH}}\begin{array}{c}OY^1\\OY^2\end{array};\qquad(V)$$

wherein:

R² is —CH₂(CH₂)$_m$W, —CH₂(C=O)R⁵, —CH₂CH₂(C=O)R⁵, —CHR⁴(CR$^{4a}$R³)$_m$W, —CHR$^{4a}$(C=O)R⁵, —CHR⁴CHR$^{4a}$(C=O)R⁵, —CHP$^{4a}$(P=O)(OR⁶)₂, —CHR⁴CHR$^{4a}$(P=O)(OR⁶)₂, —CHR$^{4a}$SO₂NH₂, —CHR⁴CHR$^{4a}$SO₂NH₂, —CHR$^{4a}$SO₃R⁶, —CHR⁴CHR$^{4a}$SO₃R⁶;

—CH₂—CH$\begin{array}{c}O\\|\\O\end{array}$ ; or —CH₂—CH$\begin{array}{c}O\\|\\O\end{array}$ ;

R³ is H, F, Cl or Br;
m is 0–4;
W is —CH₂F, —CHF₂, —CF₃, —CH₂Cl, —CHCl₂, or —CCl₃;
R⁴ and R$^{4a}$ are independently H or C₁–C₆ alkyl, aryl, or aryl-C₁–C₆ alkyl-;
R⁵ is C₁–C₆ alkyl, aryl, aryl-C₁–C₆ alkyl-, —OR⁶, —NH₂, —N(R⁶)₂, or —NHR⁶;
R⁶ is C₁–C₆ alkyl, aryl, or aryl-C₁–C₆ alkyl-; and
OY¹ and OY² are independently selected from:
 b) C₁–C₈ alkoxy, and
 when taken together with B, OY¹ and OY² form:
  c) a cyclic boronic ester where said cyclic boronic ester contains from 2 to 20 carbon atoms, and, optionally, 1, 2, or 3 heteroatoms which can be N, S, or O;

said process comprising:

(1) contacting a compound of Formula (I):

$$Ar-S-\underset{H_2}{C}-B\begin{array}{c}OY^1\\OY^2\end{array};\qquad(I)$$

wherein Ar is aryl;
with a hindered base followed by addition of a hydrocarbon containing an electrophilic center selected from:
L—CH₂(CH₂)$_m$W,
L—CH₂(C=O)R⁵,
CH₂=CH₂(C=O)R⁵,
L—CHR⁴(CR$^{4a}$R³)$_m$W,
L—CHR$^{4a}$(C=O)R⁵,
CHR⁴=CHR$^{4a}$(C=O)R⁵,
L—CHR$^{4a}$(P=O)(OR⁶)₂,
CHR⁴=CHR$^{4a}$(P=O)(OR⁶)₂,
L—CHR$^{4a}$SO₂NH₂,
CHR⁴=CHR$^{4a}$SO₂NH₂,
L—CHR$^{4a}$SO₃R⁶,
CHR⁴=CHR$^{4a}$SO₃R⁶;

L—H₂C—HC$\begin{array}{c}O\\|\\O\end{array}$ ; and L—H₂C—HC$\begin{array}{c}O\\|\\O\end{array}$ ;

to form a compound of Formula (II):

$$Ar-S-\underset{\underset{R^2}{|}}{CH}-B\begin{array}{c}OY^1\\OY^2\end{array};\qquad(II)$$

wherein L is a leaving group;

(2) contacting the compound of Formula (II) with an alkylating agent to form a compound of Formula (III):

$$Ar-\underset{\underset{R^2}{|}}{\overset{R^8\;\oplus}{S}}-\underset{}{CH}-B\begin{array}{c}OY^1\\OY^2\end{array};\qquad(III)$$

wherein R⁸ is C₁–C₆ alkyl;

(3) contacting the compound of Formula (III) with a metal halide M—X to form a compound of Formula (IV):

$$X-\underset{\underset{R^2}{|}}{CH}-B\begin{array}{c}OY^1\\OY^2\end{array};\qquad(IV)$$

wherein X is halogen; M is an alkali metal or an alkaline-earth metal; and (4) aminating the compound of Formula (IV) by either
 (i) contacting the compound of Formula (IV) with NaN₃ followed by addition of a hydrogenation agent to form the compound of Formula (V); or (ii) contacting the compound of Formula (IV) wherein R$^2$ is —CH$_2$(CH$_2$)$_m$W or —CHR$^4$(CR$^{4a}$R$^3$)$_m$W; with lithium hexamethyldisilazane followed addition of a strong acid; to form the compound of Formula (V);

or alternatively, Step (2) may be followed by (5) aminating the compound of Formula (III) by either
  (i) contacting the compound of Formula (III) with NaN$_3$ followed by addition of a hydrogenation agent to form a compound of Formula (V); or
  (ii) contacting the compound of Formula (III) wherein R$^2$ is —CH$_2$(CH$_2$)$_m$W or —CHR$^4$(CR$^{4a}$R$^3$)$_m$W; with lithium hexamethyldisilazane followed addition of a strong acid; to form a compound of Formula (V).

2. A process according to claim 1 for the synthesis of a compound of Formula (V) wherein:

R$^2$ is —CH$_2$(CH$_2$)$_m$W, —CH$_2$(C=O)R$^5$, or —CH$_2$CH$_2$(C=O)R$^5$;

m is 0–2;

W is —CH$_2$F, —CHF$_2$, —CF$_3$, —CH$_2$Cl, —CHCl$_2$, or —CCl$_3$;

R$^5$ is C$_1$–C$_6$ alkyl, aryl, aryl-C$_1$–C$_6$ alkyl-, —OR$^6$, —NH$_2$, —N(R$^6$)$_2$, or —NHR$^6$;

R$^6$ is C$_1$–C$_6$ alkyl, aryl, or aryl-C$_1$–C$_6$ alkyl-; and

OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

(I)

with a hindered base followed by a hydrocarbon containing an electrophilic center selected from:

L—CH$_2$(CH$_2$)$_m$W,
L—CH$_2$(C=O)R$^5$, and
CH$_2$=CH$_2$(C=O)R$^5$;

to form a compound of Formula (II):

(II)

wherein L is a leaving group selected from:
I, Br, Cl, methylsulfonyloxy, p-toluylsulfonyloxy and trifluoromethylsulfonyloxy;

(2) contacting the compound of Formula (II) with an alkylating agent to form a compound of Formula (III):

(III)

wherein R$^8$ is C$_1$–C$_6$ alkyl;

(3) contacting the compound of Formula (III) with a metal halide M—X to form a compound of Formula (IV):

(IV)

wherein X is halogen; M is a alkali metal or an alkaline-earth metal; and (4) aminating the compound of Formula (IV) by either
  (i) contacting the compound of Formula (IV) with NaN$_3$ followed by addition of a hydrogenation agent to form the compound of Formula (V); or
  (ii) contacting the compound of Formula (IV) wherein R$^2$ is —CH$_2$(CH$_2$)$_m$W; with lithium hexamethyldisilazane followed addition of a strong acid; to form the compound of Formula (V);

or alternatively, Step (2) may be followed by (5) aminating the compound of Formula (III) by either
  (i) contacting the compound of Formula (III) with NaN$_3$ followed by addition of a hydrogenation agent to form the compound of Formula (V); or
  (ii) contacting the compound of Formula (III) wherein R$^2$ is —CH$_2$(CH$_2$)$_m$W; with lithium hexamethyldisilazane followed addition of a strong acid; to form the compound of Formula (V).

3. A process according to claim 2 for the synthesis of a compound of Formula (V) wherein:

R$^2$ is —CH$_2$(CH$_2$)$_m$W, —CH$_2$(C=O)OR$^6$, or —CH$_2$CH$_2$(C=O)OR$^6$;

m is 0–2;

W is —CH$_2$F, —CHF$_2$, —CF$_3$, —CH$_2$Cl, —CHCl$_2$, or —CCl$_3$;

R$^6$ is C$_1$–C$_6$ alkyl, aryl, or aryl-C$_1$–C$_6$ alkyl-; and

OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

(I)

with a hindered base selected from:
lithium diisopropylamide, lithium 2,2,6,6-tetramethylpiperidine, lithium hexamethyldisilazane and n-butyllithium;

followed by a hydrocarbon containing an electrophilic center selected from:
L—CH$_2$(CH$_2$)$_m$W,
L—CH$_2$(C=O) OR$^6$, and
CH$_2$=CH$_2$(C=O)OR$^6$;
to form a compound of Formula (II):

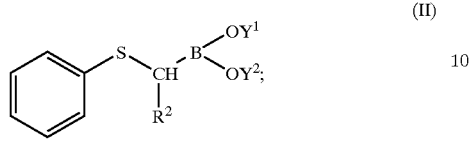
(II)

wherein L is a leaving group selected from:
I, Br, Cl, methylsulfonyloxy, p-toluylsulfonyloxy and trifluoromethylsulfonyloxy;

(2) contacting the compound of Formula (II) with an alkylating agent selecting from:
C$_1$–C$_6$ alkyl halides, trimethyloxonium tetrafluoroborate, dimethylsulfate and methyltriflate;
to form a compound of Formula (III):

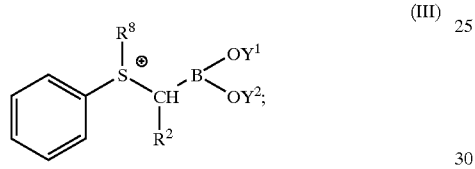
(III)

wherein R$^8$ is C$_1$–C$_6$ alkyl;

(3) contacting the compound of Formula (III) with a metal halide M—X selected from sodium iodide, lithium bromide and potassium iodide;
to form a compound of Formula (IV):

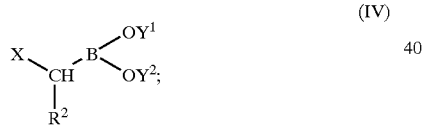
(IV)

wherein X is I or Br; and (4) aminating the compound of Formula (IV) by either
(i) contacting the compound of Formula (IV) with NaN$_3$ followed by contacting a hydrogenation agent selected from:
H$_2$/Pd—C; and
SnCl$_2$ in methanol;
to form the compound of Formula (V); or
(ii) contacting the compound of Formula (IV) wherein R$^2$ is —CH$_2$(CH$_2$)$_m$W lithium hexamethyldisilazane followed by contacting a strong acid selected from:
anhydrous HCl; and
trifluoroacetic acid;
to form the compound of Formula (V).

4. A process according to claim 3 for the synthesis of a compound of Formula (V) wherein:
R$^2$ is —CH$_2$(CH$_2$)$_m$W, —CH$_2$(C=O)OR$^6$, or —CH$_2$CH$_2$(C=O)OR$^6$;
m is 0–2;
W is —CH$_2$F, —CHF$_2$, —CF$_3$, —CH$_2$Cl, —CHCl$_2$, or —CCl$_3$;
R$^6$ is C$_1$–C$_6$ alkyl, aryl, or aryl-C$_1$–C$_6$ alkyl-; and OY$^1$ and OY$^2$ are taken together with B to form a cyclic boronic ester where said cyclic boronic ester is formed from the group: pinanediol and pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

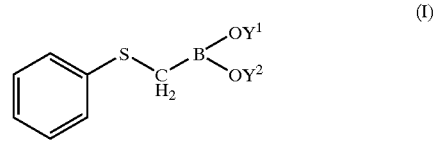
(I)

with a hindered base selected from:
lithium diisopropylamide, lithium 2,2,6,6-tetramethylpiperidine and lithium hexamethyldisilazane;
followed by a hydrocarbon containing an electrophilic center selected from:
L—CH$_2$(CH$_2$)$_m$W,
L—CH$_2$(C=O)OR$^6$, and
CH$_2$=CH$_2$(C=O)OR$^6$;
to form a compound of Formula (II):

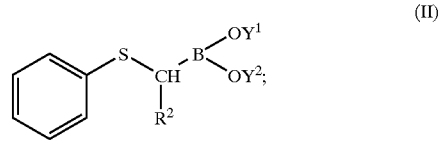
(II)

wherein L is I or Br;

(2) contacting the compound of Formula (II) with an alkylating agent selected from:
methyl iodide, ethyl iodide and trimethyloxonium tetrafluoroborate;
to form a compound of Formula (III):

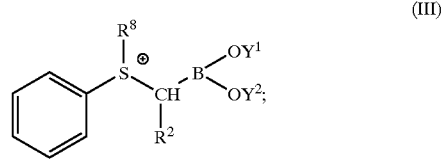
(III)

wherein R$^8$ is methyl or ethyl;

(3) contacting the compound of Formula (III) with sodium iodide to form a compound of Formula (IV):

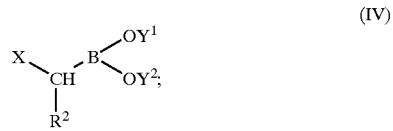
(IV)

wherein X is I; and (4) aminating the compound of Formula (IV) by either
(i) contacting the compound of Formula (IV) with NaN$_3$ followed by addition of H$_2$/Pd—C to form the compound of Formula (V); or (ii) contacting the compound of Formula (IV) wherein R² is —CH₂(CH₂)ₘW; with lithium hexamethyldisilazane followed addition of a strong acid selected from:
anhydrous HCl; and
trifluoroacetic acid;
to form the compound of Formula (V).

5. A process according to claim 2 for the synthesis of a compound of Formula (V-1):

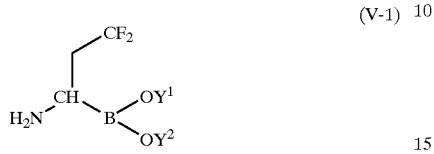

wherein OY¹ and OY² are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;
said process comprising:
(1) contacting a compound of Formula (I):

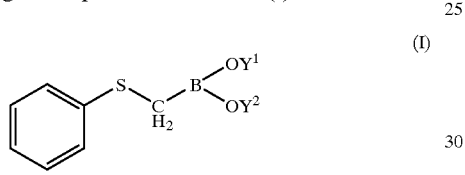

with a hindered base followed by L—CH₂CHF₂;
to form a compound of Formula (II-1):

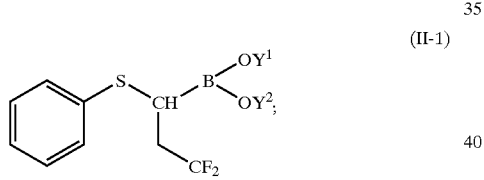

wherein L is a leaving group;
(2) contacting the compound of Formula (II-1) with an alkylating agent to form a compound of Formula (III-1):

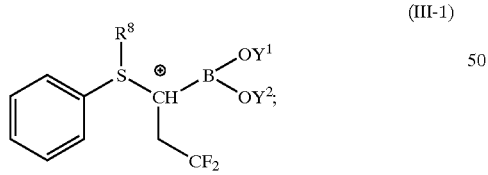

wherein R⁸ is C₁–C₆ alkyl;
(3) contacting the compound of Formula (III-1) with a metal halide M—X to form a compound of Formula (IV-1):

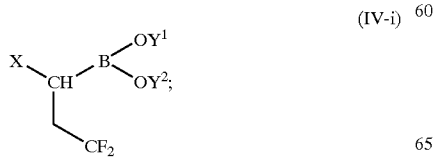

wherein X is halogen; M is a alkali metal or an alkaline-earth metal; and
(4) aminating the compound of Formula (IV-1) by either
(i) contacting the compound of Formula (IV-1) with NaN₃ followed by addition of a hydrogenation agent to form the compound of Formula (V-1); or
(ii) contacting the compound of Formula (IV-1) with lithium hexamethyldisilazane followed addition of a strong acid; to form the compound of Formula (V-1);
or alternatively, Step (2) may be followed by
(5) aminating the compound of Formula (III-1) by either
(i) contacting the compound of Formula (III-1) with NaN₃ followed by addition of a hydrogenation agent to form the compound of Formula (V-1); or
(ii) contacting the compound of Formula (III-1) with lithium hexamethyldisilazane followed addition of a strong acid; to form the compound of Formula (V-1).

6. A process according to claim 5 for the synthesis of a compound of Formula (V-1) wherein:
OY¹ and OY² are taken together with B to form a cyclic boronic ester where said cyclic boronic ester is formed from the group: pinanediol and pinacol;
said process comprising:
(1) contacting a compound of Formula (I):

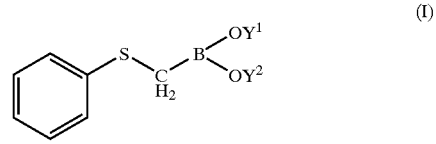

with a hindered base selected from:
lithium diisopropylamide, lithium 2,2,6,6-tetramethylpiperidine, lithium hexamethyldisilazane and n-butyllithium;
followed by L—CH₂CHF₂;
to form a compound of Formula (II-1):

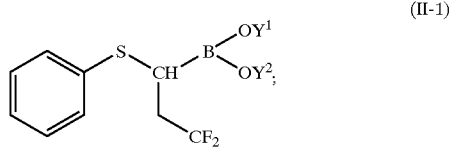

wherein L is a leaving group selected from:
I, Br, Cl, methylsulfonyloxy, p-toluylsulfonyloxy and trifluoromethylsulfonyloxy;
(2) contacting the compound of Formula (II-1) with an alkylating agent selected from:
C₁–C₆ alkyl halides, trimethyloxonium tetrafluoroborate, dimethylsulfate and methyltriflate;
to form a compound of Formula (III-1):

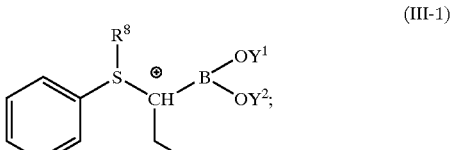

wherein R⁸ is C₁–C₆ alkyl;

(3) contacting the compound of Formula (III-1) with a metal halide M—X selected from sodium iodide, lithium bromide and potassium iodide;

to form a compound of Formula (IV-1):

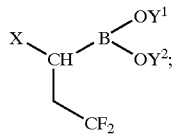

(IV-i)

wherein X is I or Br; and (4) aminating the compound of Formula (IV-1) by either (i) contacting the compound of Formula (IV-1) with NaN$_3$ followed by addition of a hydrogenation agent selected from:

H$_2$/Pd—C; and

SnCl$_2$ in methanol;

to form the compound of Formula (V-1); or (ii) contacting the compound of Formula (IV-1) with lithium hexamethyldisilazane followed addition of a strong acid a strong acid selected from:

anhydrous HCl; and trifluoroacetic acid;

to form the compound of Formula (V-1).

7. A process according to claim 6 for the synthesis of a compound of Formula (V-1) comprising:

(1) contacting a compound of Formula (I):

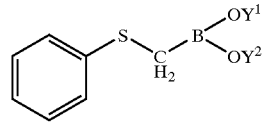

(I)

with a hindered base selected from:

lithium diisopropylamide, lithium 2,2,6,6-tetramethylpiperidine and lithium hexamethyldisilazane;

followed by L—CH$_2$CHF$_2$;

to form a compound of Formula (II-1):

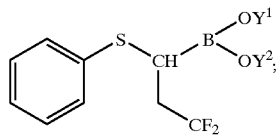

(II-1)

wherein L is I or Br;

(2) contacting the compound of Formula (II-1) with an alkylating agent selected from:

methyl iodide, ethyl iodide and trimethyloxonium tetrafluoroborate;

to form a compound of Formula (III-1):

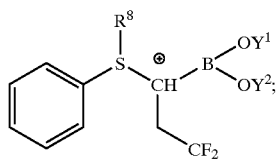

(III-1)

wherein R$^8$ is methyl or ethyl;

(3) contacting the compound of Formula (III-1) with sodium iodide to form a compound of Formula (IV-1):

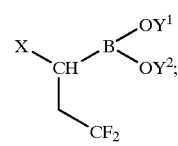

(IV-i)

wherein X is I; and (4) aminating the compound of Formula (IV-1) by either (i) contacting the compound of Formula (IV-1) with NaN$_3$ followed by addition of H$_2$/Pd—C to form the compound of Formula (V-1); or (ii) contacting the compound of Formula (IV-1) with lithium hexamethyldisilazane followed addition of a strong acid a strong acid selected from:

anhydrous HCl; and trifluoroacetic acid;

to form the compound of Formula (V-1).

8. A process according to claim 2 for the synthesis of a compound of Formula (V-2):

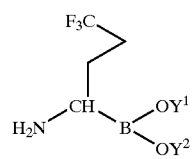

(V-2)

wherein OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

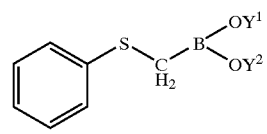

(I)

with a hindered base followed by L—CH$_2$CH$_2$CF$_3$;
to form a compound of Formula (II-2):

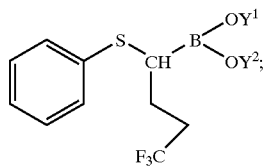

(II-2)

wherein L is a leaving group;

(2) contacting the compound of Formula (II-2) with an alkylating agent to form a compound of Formula (III-2):

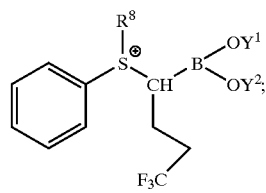

(III-2)

wherein R$^8$ is C$_1$–C$_6$ alkyl;

(3) contacting the compound of Formula (III-2) with a metal halide M—X to form a compound of Formula (IV-2):

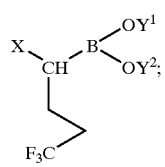

(IV-2)

wherein X is halogen; M is a alkali metal or an alkaline-earth metal; and (4) aminating the compound of Formula (IV-2) by either
  (i) contacting the compound of Formula (IV-2) with NaN$_3$ followed by addition of a hydrogenation agent to form the compound of Formula (V-2); or
  (ii) contacting the compound of Formula (IV-2) with lithium hexamethyldisilazane followed addition of a strong acid; to form the compound of Formula (V-2);

or alternatively, Step (2) may be followed by (5) aminating the compound of Formula (III-2) by either
  (i) contacting the compound of Formula (III-2) with NaN$_3$ followed by addition of a hydrogenation agent to form the compound of Formula (V-2); or
  (ii) contacting the compound of Formula (III-2) with lithium hexamethyldisilazane followed addition of a strong acid; to form the compound of Formula (V-2).

9. A process according to claim 8 for the synthesis of a compound of Formula (V-2) wherein:
  OY$^1$ and OY$^2$ are taken together with B to form a cyclic boronic ester where said cyclic boronic ester is formed from the group: pinanediol and pinacol;
said process comprising:
(1) contacting a compound of Formula (I):
(2)

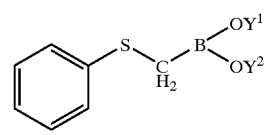

(I)

with a hindered base selected from:
  lithium diisopropylamide, lithium 2,2,6,6-tetramethylpiperidine, lithium hexamethyldisilazane and n-butyllithium;
followed by L—CH$_2$CH$_2$CF$_3$;
to form a compound of Formula (II-2):

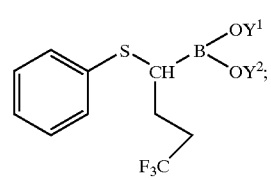

(II-2)

L is a leaving group selected from:
  I, Br, Cl, methylsulfonyloxy, p-toluylsulfonyloxy and trifluoromethylsulfonyloxy;
(2) contacting the compound of Formula (II-2) with an alkylating agent selected from:
  C$_1$–C$_6$ alkyl halides, trimethyloxonium tetrafluoroborate, dimethylsulfate and methyltriflate;
to form a compound of Formula (III-2):

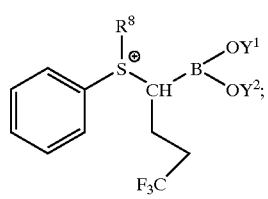

(III-2)

wherein R$^8$ is C$_1$–C$_6$ alkyl;
(3) contacting the compound of Formula (III-2) with a metal halide M—X selected from sodium iodide, lithium bromide and potassium iodide;
to form a compound of Formula (IV-2):

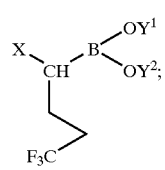

(IV-2)

wherein X is I or Br; and
(4) aminating the compound of Formula (IV-2) by either
  (i) contacting the compound of Formula (IV-2) with NaN$_3$ followed by addition of a hydrogenation agent selected from:
    H$_2$/Pd—C; and
    SnCl$_2$ in methanol;
  to form the compound of Formula (V-2); or
  (ii) contacting the compound of Formula (IV-2) with lithium hexamethyldisilazane followed addition of a strong acid a strong acid selected from:
anhydrous HCl; and
trifluoroacetic acid;
to form the compound of Formula (V-2).

10. A process according to claim 9 for the synthesis of a compound of Formula (V-2) comprising:

(1) contacting a compound of Formula (I):

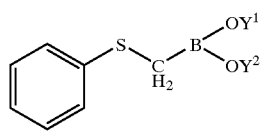

with a hindered base selected from:
lithium diisopropylamide, lithium 2,2,6,6-tetramethylpiperidine and lithium hexamethyldisilazane;
followed by L—CH$_2$CH$_2$CF$_3$;
to form a compound of Formula (II-2):

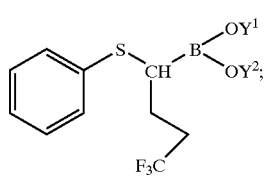

wherein L is I or Br;

(2) contacting the compound of Formula (II-2) with an alkylating agent selected from:
methyl iodide, ethyl iodide and trimethyloxonium tetrafluoroborate;
to form a compound of Formula (III-2):

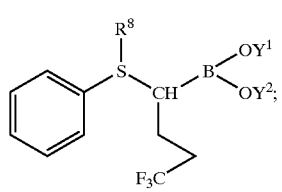

wherein R$^8$ is methyl or ethyl;

(3) contacting the compound of Formula (III-2) with sodium iodide to form a compound of Formula (IV-2):

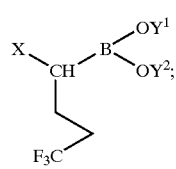

wherein X is I; and (4) aminating the compound of Formula (IV-2) by either
(i) contacting the compound of Formula (IV-2) with NaN$_3$ followed by addition of H$_2$/Pd—C to form the compound of Formula (V-2); or (ii) contacting the compound of Formula (IV-2) with lithium hexamethyldisilazane followed addition of a strong acid a strong acid selected from:
anhydrous HCl; and
trifluoroacetic acid;
to form the compound of Formula (V-2).

11. A process according to claim 2 for the synthesis of a compound of Formula (V-3):

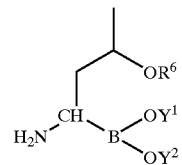

wherein
R$^6$ is Me or t-Bu; and
OY$^1$ and OY$^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;
said process comprising:

(1) contacting a compound of Formula (I):

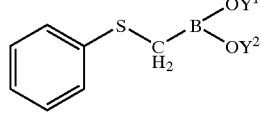

with a hindered base followed by L—CH$_2$C(=O)OR$^6$;
to form a compound of Formula (II-3):

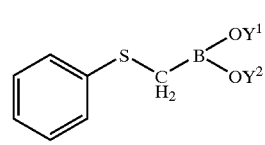

wherein L is a leaving group;

(2) contacting the compound of Formula (II-3) with an alkylating agent to form a compound of Formula (III-3):

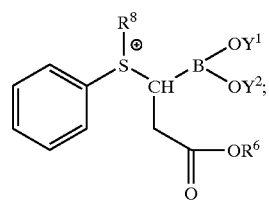

wherein R$^8$ is C$_1$–C$_6$ alkyl;

(3) contacting the compound of Formula (III-3) with a metal halide M—X to form a compound of Formula (IV-3):

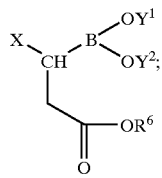

(IV-3)

wherein X is halogen; M is a alkali metal or an alkaline-earth metal; and (4) aminating the compound of Formula (IV-3) by contacting the compound of Formula (IV-3) with NaN$_3$ followed by addition of a hydrogenation agent to form the compound of Formula (V-3); or or alternatively, Step (2) may be followed by (5) aminating the compound of Formula (III-3) by contacting the compound of Formula (III-3) with NaN$_3$ followed by addition of a hydrogenation agent to form the compound of Formula (V-3).

12. A process according to claim 11 for the synthesis of a compound of Formula (V-3) wherein:

R$^6$ is Me or t-Bu; and

OY$^1$ and OY$^2$ are taken together with B to form a cyclic boronic ester where said cyclic boronic ester is formed from the group: pinanediol and pinacol;

said process comprising:

(1) contacting a compound of Formula (I):

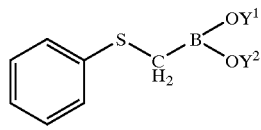

(I)

with a hindered base selected from:
lithium diisopropylamide, lithium 2,2,6,6-tetramethylpiperidine, lithium hexamethyldisilazane and n-butyllithium;
followed by L—CH$_2$C(=O)OR$^6$;
to form a compound of Formula (II-3):

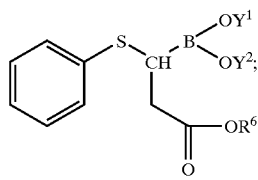

(II-3)

wherein L is a leaving group selected from:
I, Br, Cl, methylsulfonyloxy, p-toluylsulfonyloxy and trifluoromethylsulfonyloxy;

(2) contacting the compound of Formula (II-3) with an alkylating agent selected from:
C$_1$–C$_6$ alkyl halides, trimethyloxonium tetrafluoroborate, dimethylsulfate and methyltriflate;

to form a compound of Formula (III-3):

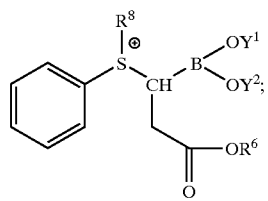

(III-3)

wherein R$^8$ is C$_1$–C$_6$ alkyl;

(3) contacting the compound of Formula (III-3) with a metal halide M—X selected from sodium iodide, lithium bromide and potassium iodide;

to form a compound of Formula (IV-3):

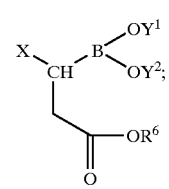

(IV-3)

wherein X is I or Br; and (4) aminating the compound of Formula (IV-3) by contacting the compound of Formula (IV-3) with NaN$_3$ followed by addition of a hydrogenation agent selected from:
H$_2$/Pd—C; and
SnCl$_2$ in methanol;
to form the compound of Formula (V-3).

13. A process according to claim 12 for the synthesis of a compound of Formula (V-3) comprising:

(1) contacting a compound of Formula (I):

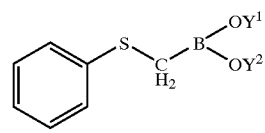

(I)

with a hindered base selected from:
lithium diisopropylamide, lithium 2,2,6,6-tetramethylpiperidine and lithium hexamethyldisilazane;
followed by L—CH$_2$C(=O)OR$^6$;
to form a compound of Formula (II-3):

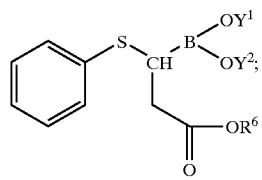

(II-3)

wherein L is I or Br;

(2) contacting the compound of Formula (II-3) with an alkylating agent selected from:
methyl iodide, ethyl iodide and trimethyloxonium tetrafluoroborate;

to form a compound of Formula (III-3):

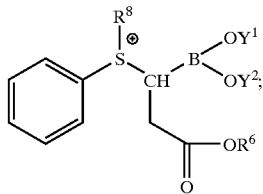

(III-3)

wherein R⁸ is methyl or ethyl;

(3) contacting the compound of Formula (III-3) with sodium iodide to form a compound of Formula (IV-3):

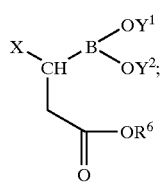

(IV-3)

wherein X is I; and (4) aminating the compound of Formula (IV-3) by contacting the compound of Formula (IV-3) with NaN₃ followed by addition of H₂/Pd—C to form the compound of Formula (V-3).

14. A process according to claim 2 for the synthesis of a compound of Formula (V-4):

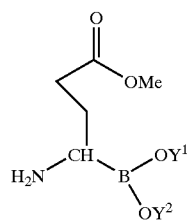

(V-4)

wherein $OY^1$ and $OY^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

said process comprising:

(1) contacting a compound of Formula (I):

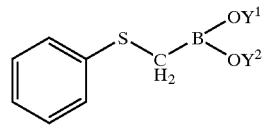

(I)

with a hindered base followed CH₂=CH(C=O)OMe; to form a compound of Formula (II-4):

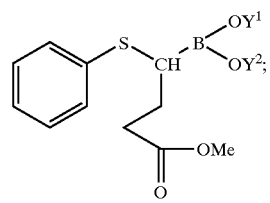

(II-4)

(2) contacting the compound of Formula (II-4) with an alkylating agent to form a compound of Formula (III-4):

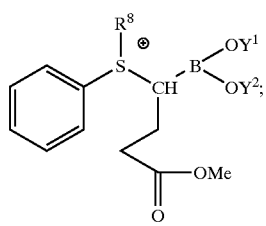

(III-4)

wherein R⁸ is C₁–C₆ alkyl;

(3) contacting the compound of Formula (III-4) with a metal halide M—X to form a compound of Formula (IV-4):

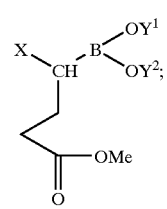

(IV-4)

wherein X is halogen; M is a alkali metal or an alkaline-earth metal; and (4) aminating the compound of Formula (IV-4) by contacting the compound of Formula (IV-4) with NaN₃ followed by addition of a hydrogenation agent to form the compound of Formula (V-4); or or alternatively, Step (2) may be followed by (5) aminating the compound of Formula (III-4) by contacting the compound of Formula (III-4) with NaN₃ followed by addition of a hydrogenation agent to form the compound of Formula (V-4).

15. A process according to claim 14 for the synthesis of a compound of Formula (V-4) wherein:

$OY^1$ and $OY^2$ are taken together with B to form a cyclic boronic ester where said cyclic boronic ester is formed from the group: pinanediol and pinacol;

said process comprising:

(1) contacting a compound of Formula (I):

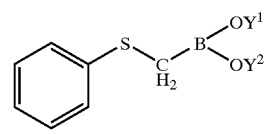

(I)

with a hindered base selected from:

lithium diisopropylamide, lithium 2,2,6,6-tetramethylpiperidine, lithium hexamethyldisilazane and n-butyllithium;

followed by by CH$_2$=CH(C=O)OMe;

to form a compound of Formula (II-4):

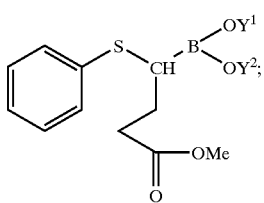

(2) contacting the compound of Formula (II-4) with an alkylating agent selected from:

C$_1$–C$_6$ alkyl halides, trimethyloxonium tetrafluoroborate, dimethylsulfate and methyltriflate;

to form a compound of Formula (III-4):

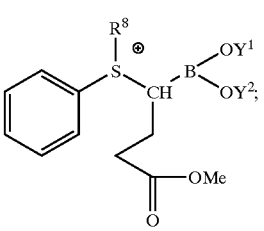

wherein R$^8$ is C$_1$–C$_6$ alkyl;

(3) contacting the compound of Formula (III-4) with a metal halide M—X selected from sodium iodide, lithium bromide and potassium iodide;

to form a compound of Formula (IV-4):

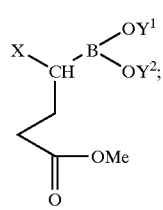

wherein X is I or Br; and (4) aminating the compound of Formula (IV-4) by contacting the compound of Formula (IV-4) with NaN$_3$ followed by addition of a hydrogenation agent selected from:

H$_2$/Pd—C; and

SnCl$_2$ in methanol;

to form the compound of Formula (V-4).

16. A process according to claim 15 for the synthesis of a compound of Formula (V-3) comprising:

(1) contacting a compound of Formula (I):

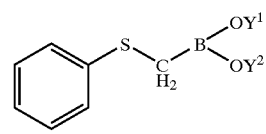

with a hindered base selected from:

lithium diisopropylamide, lithium 2,2,6,6-tetramethylpiperidine and lithium hexamethyldisilazane;

followed by CH$_2$=CH(C=O)OMe;

L is I or Br;

to form a compound of Formula (II-4):

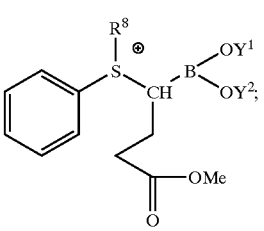

(2) contacting the compound of Formula (II-4) with an alkylating agent selected from:

methyl iodide, ethyl iodide and trimethyloxonium tetrafluoroborate;

to form a compound of Formula (III-4):

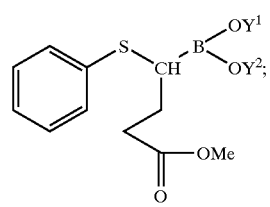

wherein R$^8$ is methyl or ethyl;

(3) contacting the compound of Formula (III-4) with sodium iodide to form a compound of Formula (IV-4):

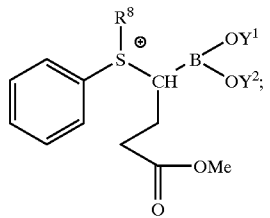

wherein X is I; and (4) aminating the compound of Formula (IV-4) by contacting the compound of Formula (IV-4) with NaN$_3$ followed by addition of H$_2$/Pd—C to form the compound of Formula (V-4).

17. A compound of Formula (V-a):

$$R^1\underset{H}{N}\text{-CH}(R^2)\text{-B}(OY^1)(OY^2)$$ (V-a)

wherein:

$R^1$ is H or $C_1$–$C_6$ alkyl;

$R^2$ is —$CH_2(CH_2)_m$W, —$CH_2(C=O)R^5$, —$CH_2CH_2(C=O)R^5$, —$CHR^4(CR^{4a}R^3)_m$W, —$CHR^{4a}(C=O)R^5$, —$CHR^4CHR^{4a}(C=O)R^5$, —$CHR^{4a}(P=O)(OR^6)_2$, —$CHR^4CHR^{4a}(P=O)(OR^6)_2$, —$CHR^{4a}SO_2NH_2$, —$CHR^4CHR^{4a}SO_2NH_2$, —$CHR^{4a}SO_3R^6$, —$CHR^4CHR^{4a}SO_2NH_2$;

—$CH_2$—CH(—O—CH$_2$—CH$_2$—O—); or —$CH_2$—CH(—O—CH$_2$—CH$_2$—CH$_2$—O—);

$R^3$ is H, F, Cl or Br;

m is 0–4;

W is —$CH_2F$, —$CHF_2$, —$CF_3$, —$CHCl_2$, or —$CCl_3$;

$R^4$ and $R^{4a}$ are independently H or $C_1$–$C_6$ alkyl, aryl, or aryl-$C_1$–$C_6$ alkyl-;

$R^5$ is $C_1$–$C_6$ alkyl, aryl, aryl-$C_1$–$C_6$ alkyl-, —$OR^6$, —$NH_2$, —$N(R^6)_2$, or —$NHR^6$;

$R^6$ is H, $C_1$–$C_6$ alkyl, aryl, or aryl-$C_1$–$C_6$ alkyl-; and $OY^1$ and $OY^2$ are independently selected from:
b) $C_1$–$C_8$ alkoxy, and
when taken together with B, $OY^1$ and $OY^2$ form:
c) a cyclic boronic ester where said cyclic boronic ester contains from 2 to 20 carbon atoms, and, optionally, 1, 2, or 3 heteroatoms which can be N, S, or O.

18. A compound of claim 17 wherein:

$R^1$ is H or $C_1$–$C_6$ alkyl;

$R^2$ is —$CH_2CHF_2$, —$CH_2CH_2CF_3$, —$CH_2(C=O)R^5$, or —$CH_2CH_2$—$(C=O)R^5$;

$R^5$ is $C_1$–$C_6$ alkyl, aryl, aryl-$C_1$–$C_6$ alkyl-, —$OR^6$, or —$N(R^6)_2$;

$R^6$ is H, $C_1$–$C_6$ alkyl, aryl, or aryl-$C_1$–$C_6$ alkyl-; and $OY^1$ and $OY^2$ are independently selected from:
a) —OH,
b) $C_1$–$C_8$ alkoxy, and
when taken together with B, $OY^1$ and $OY^2$ form:
c) a cyclic boronic ester where said cyclic boronic ester contains from 2 to 14 carbon atoms, and, optionally, 1, 2, or 3 heteroatoms which can be N, S, or O.

19. A compound of claim 17 wherein:

$R^1$ is H;

$R^2$ is —$CH_2CHF_2$, —$CH_2CH_2CF_3$, —$CH_2(C=O)OR^6$, or —$CH_2CH_2$—$(C=O)OR^6$;

$R^6$ is H or $C_1$–$C_6$ alkyl; and $OY^1$ and $OY^2$ are taken together with B to form a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol.

20. A compound of claim 17 is:

1-amino-3,3-difluoropropyl boronate pinacol ester; and
1-amino-4,4,4-trifluorobutyl boronate pinanediol ester.

21. A compound of claim 17 is selected from:

1-amino-2-t-butoxycarbonylethane-1-boronate pinanediol ester;
1-amino-2-methoxycarbonylethane-1-boronate pinanediol ester;
1-amino-2-hydroxycarbonylethane-1-boronate pinanediol ester;
1-amino-3-methoxycarbonyl-propane-1-boronate pinanediol ester; and
1-amino-3-hydroxycarbonyl-propane-1-boronate pinanediol ester.

* * * * *